United States Patent
Sheppard et al.

(10) Patent No.: US 9,969,804 B2
(45) Date of Patent: May 15, 2018

(54) METHODS AND COMPOSITIONS FOR TREATING AND PREVENTING DISEASE ASSOCIATED WITH ALPHA-V BETA-8 INTEGRIN

(71) Applicant: The Regents of the University of California, Oakland, CA (US)

(72) Inventors: Dean Sheppard, Oakland, CA (US); Amha Atakilit, Oakland, CA (US); Neil Cowan Henderson, Edinburgh (GB)

(73) Assignee: The Regents of the University of California, Oakland, CA (US)

( * ) Notice: Subject to any disclaimer, the term of this patent is extended or adjusted under 35 U.S.C. 154(b) by 141 days.

(21) Appl. No.: 14/778,997

(22) PCT Filed: Apr. 1, 2014

(86) PCT No.: PCT/US2014/032550
§ 371 (c)(1),
(2) Date: Sep. 21, 2015

(87) PCT Pub. No.: WO2014/165524
PCT Pub. Date: Oct. 9, 2014

(65) Prior Publication Data
US 2016/0046717 A1    Feb. 18, 2016

Related U.S. Application Data

(60) Provisional application No. 61/807,195, filed on Apr. 1, 2013.

(51) Int. Cl.
*C07K 16/00* (2006.01)
*C07K 16/28* (2006.01)

(52) U.S. Cl.
CPC ...... *C07K 16/2839* (2013.01); *C07K 2317/33* (2013.01); *C07K 2317/567* (2013.01); *C07K 2317/76* (2013.01)

(58) Field of Classification Search
None
See application file for complete search history.

(56) References Cited

U.S. PATENT DOCUMENTS

| 5,635,601 A | * | 6/1997 | Moyle | ............. | C07K 14/70546 |
|---|---|---|---|---|---|
| | | | | | 424/139.1 |
| 2010/0291071 A1 | | 11/2010 | Matsubara et al. | | |
| 2010/0329929 A1 | | 12/2010 | Goix et al. | | |
| 2013/0064837 A1 | | 3/2013 | Nishimura et al. | | |

FOREIGN PATENT DOCUMENTS

| WO | 2007/008712 A2 | 1/2007 |
|---|---|---|
| WO | 2011/103490 A2 | 8/2011 |
| WO | WO2011103490 | * 8/2011 |

OTHER PUBLICATIONS

Eberlein et al "A human monoclonal antibody 264RAD targeting .alpha.v.beta.6 integrin reduces tumor growth and metastasis, and modulates key biomarkers in vivo" (Oncogene (2013), 32(37):4406-4416. Published online Oct. 29, 2012.*
Partial Supplementary European Search Report in EP 14778764.2 dated Oct. 6, 2016, 9 pages.
Minagawa et al., "Selective Targeting of TGF-β Activation to Treat Fibroinflammatory Airway Disease," Sci Transl Med. Jun. 18, 2014; 6(241), 30 pages.
Mu et al., "The integrin alpha-v beta-8 mediates epithelial homeostasis through MT1-MMP-dependent of TGF-beta-1," The Journal of Cell Biology, 157(3):493-507 (Apr. 2002).
Santa Cruz Biotechnology. Datasheet. "Integrin beta-8 Antibody (H-160): sc-25714." May 19, 2012 (3 pages) Retrieved from the Internet: <http://www.scht.com/datasheet-25714-integrinbeta8-h-160-antibody.html> on Aug. 20, 2014.
International Search Report and Written Opinion from International Application No. PCT/US2014/032550, dated Sep. 15, 2014.

* cited by examiner

*Primary Examiner* — Maher M Haddad
(74) *Attorney, Agent, or Firm* — Kilpatrick Townsend & Stockton LLP

(57) ABSTRACT

Antibodies (e.g., isolated antibodies) that specifically bind to human integrin β8 and inhibit adhesion of latency associated peptide (LAP) to αvβ8 are provided. In some embodiments, the antibody cross-reacts with mouse integrin β8. In some embodiments, the antibody blocks TGFβ3 activation. In some embodiments, the antibody antagonizes binding of LAP to αβ8 with an IC50 below 5 nM.

20 Claims, 13 Drawing Sheets

METHODS AND COMPOSITIONS FOR TREATING AND PREVENTING DISEASE ASSOCIATED WITH ALPHA-V BETA-8 INTEGRIN

CROSS REFERENCES TO RELATED APPLICATIONS

This application is the US National Stage entry of International Appl. No. PCT/US2014/032550, filed Apr. 1, 2014, which claims priority to U.S. Provisional Appl. No. 61/807,195, filed Apr. 1, 2013, the disclosures of each are incorporated herein in their entireties.

STATEMENT AS TO RIGHTS TO INVENTIONS MADE UNDER FEDERALLY SPONSORED RESEARCH AND DEVELOPMENT

This invention was made with government support under grant nos. R37 HL053949 and U19 AI077439 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 081906-0958641_ST25.txt, created on Sep. 21, 2015, 46,282 bytes, machine format IBM-PC, MS-Windows operating system, is hereby incorporated by reference.

BACKGROUND OF THE INVENTION

Members of the integrin family recognize a variety of spatially-restricted extracellular ligands. Classically, ligation of integrins activates cytoplasmic signals in the integrin-expressing cell and contributes to cell adhesion, migration, proliferation and survival. At least two members of this family, $\alpha v \beta 6$ and $\alpha v \beta 8$, perform an additional function, activation of latent complexes of transforming growth factor $\beta$. In effect, this process allows integrins on one cell to activate signals on adjacent (in the case of $\alpha v \beta 6$) or nearby cells (in the case of $\alpha v \beta 8$). Integrin-mediated TGF$\beta$ activation has been shown to play roles in, for example, modulating tissue fibrosis, acute lung injury and pulmonary emphysema.

BRIEF SUMMARY OF THE INVENTION

Antibodies (e.g., isolated antibodies) that specifically bind to human integrin $\beta 8$ and inhibit adhesion of latency associated peptide (LAP) to $\alpha v \beta 8$ are provided. In some embodiments, the antibody cross-reacts with mouse integrin $\beta 8$. In some embodiments, the antibody blocks TGF$\beta$ activation. In some embodiments, the antibody antagonizes binding of LAP to $\alpha v \beta 8$ with an $IC_{50}$ below 5 nM.

In some embodiments, the antibody competes for binding with an antibody selected from the group consisting of ADWA-2 (ADWA-2, ADWA-2-1 and ADWA-2-2), ADWA-8 (ADWA-8, ADWA-8-1, ADWA-8-2, ADWA-8-3), ADWA-10, ADWA-11, ADWA-13 (ADWA-13, ADWA-13-1, ADWA-13-2), ADWA-15, ADWA-16, ADWA-25, and ADWA-20.

In some embodiments, the antibody comprises the complementarity determining regions (CDR1, CDR2, and CDR3) of the heavy and light chain variable regions of an antibody selected from ADWA-2 (ADWA-2, ADWA-2-1 and ADWA-2-2), ADWA-8 (ADWA-8, ADWA-8-1, ADWA-8-2, ADWA-8-3), ADWA-10, ADWA-11, ADWA-13 (ADWA-13, ADWA-13-1, ADWA-13-2), ADWA-15, ADWA-16, ADWA-25, and ADWA-20. In some embodiments, the antibody comprises the Chothia-determined CDR1, CDR2, and CDR3 of the heavy and light chain variable regions of an antibody selected from ADWA-2 (ADWA-2, ADWA-2-1 and ADWA-2-2), ADWA-8 (ADWA-8, ADWA-8-1, ADWA-8-2, ADWA-8-3), ADWA-10, ADWA-11, ADWA-13 (ADWA-13, ADWA-13-1, ADWA-13-2), ADWA-15, ADWA-16, ADWA-25, and ADWA-20. In some embodiments, antibody comprises the Kabat-determined CDR1, CDR2, and CDR3 of the heavy and light chain variable regions of an antibody selected from ADWA-2 (ADWA-2, ADWA-2-1 and ADWA-2-2), ADWA-8 (ADWA-8, ADWA-8-1, ADWA-8-2, ADWA-8-3), ADWA-10, ADWA-11, ADWA-13 (ADWA-13, ADWA-13-1, ADWA-13-2), ADWA-15, ADWA-16, ADWA-25, and ADWA-20.

In some embodiments, the antibody comprises the heavy and light chain variable regions of an antibody selected from ADWA-2 (ADWA-2, ADWA-2-1 and ADWA-2-2), ADWA-8 (ADWA-8, ADWA-8-1, ADWA-8-2, ADWA-8-3), ADWA-10, ADWA-11, ADWA-13 (ADWA-13, ADWA-13-1, ADWA-13-2), ADWA-15, ADWA-16, ADWA-25, and ADWA-20.

In some embodiments, the antibody comprises the heavy chain CDRs (Chothia or Kabat) shown in SEQ ID NOs:23-25, and the light chain CDRs shown in SEQ ID NOs:46-48. In some embodiments, the antibody comprises the heavy chain CDRs (Chothia or Kabat) shown in SEQ ID NOs:23, 26, and 25, and the light chain CDRs shown in SEQ ID NOs:46-48. In some embodiments, the antibody comprises the heavy chain CDRs (Chothia or Kabat) shown in SEQ ID NOs:27-29, and the light chain CDRs shown in SEQ ID NOs:46, 49, and 50. In some embodiments, the antibody comprises the heavy chain CDRs (Chothia or Kabat) shown in SEQ ID NOs:30-32, and the light chain CDRs shown in SEQ ID NOs:51-53. In some embodiments, the antibody comprises the heavy chain CDRs (Chothia or Kabat) shown in SEQ ID NOs:33-35, and the light chain CDRs shown in SEQ ID NOs:54-56. In some embodiments, the antibody comprises the heavy chain CDRs (Chothia or Kabat) shown in SEQ ID NOs:36-38, and the light chain CDRs shown in SEQ ID NOs:57-59. In some embodiments, the antibody comprises the heavy chain CDRs (Chothia or Kabat) shown in SEQ ID NOs:36, 39, and 38, and the light chain CDRs shown in SEQ ID NOs:57-59. In some embodiments, the antibody comprises the heavy chain CDRs (Chothia or Kabat) shown in SEQ ID NOs:40-42, and the light chain CDRs shown in SEQ ID NOs:60-62. In some embodiments, the antibody comprises the heavy chain CDRs (Chothia or Kabat) shown in SEQ ID NOs:43-45, and the light chain CDRs shown in SEQ ID NOs:63-65.

Any of the antibodies described herein can include one or more human framework region (e.g., 1, 2, 3, or 4 FRs). In some embodiments, the one or more human framework region includes at least one back mutation. Pharmaceutical compositions comprising any of the antibodies described herein are also provided.

Isolated nucleic acid encoding any of the antibodies described herein are also provided (e.g., SEQ ID NOs:66-87, and conservative variants thereof). Expression vectors comprising the nucleic acid are also provided. Isolated host cells comprising the vectors are also provided.

Also provided are methods of reducing TGFβ activation in a human in need thereof. In some embodiments, the methods comprise administering a sufficient amount of the antibody as described herein to the human, thereby reducing TGFβ activation in the human. In some embodiments, the human has a disease selected from the group consisting of asthma, multiple sclerosis or acute lung injury and at least one symptom of the disease is ameliorated by the reduced TGFβ activation. In some embodiments, the human has a disease selected from the group consisting of rheumatoid arthritis, psoriasis and chronic obstructive pulmonary disease and at least one symptom of the disease is ameliorated by the reduced TGFβ activation.

Also provided is a method of detecting the presence or quantity of integrin β8 in a biological sample. In some embodiments, the method comprises contacting the biological sample with the antibody as described herein and detecting the presence, absence, or quantity of the antibody specifically bound to β8 in the sample. In some embodiments, the antibody is linked to a detectable label, wherein the label is fluorescent.

DETAILED DESCRIPTION OF THE INVENTION

I. Introduction

Figure 1:
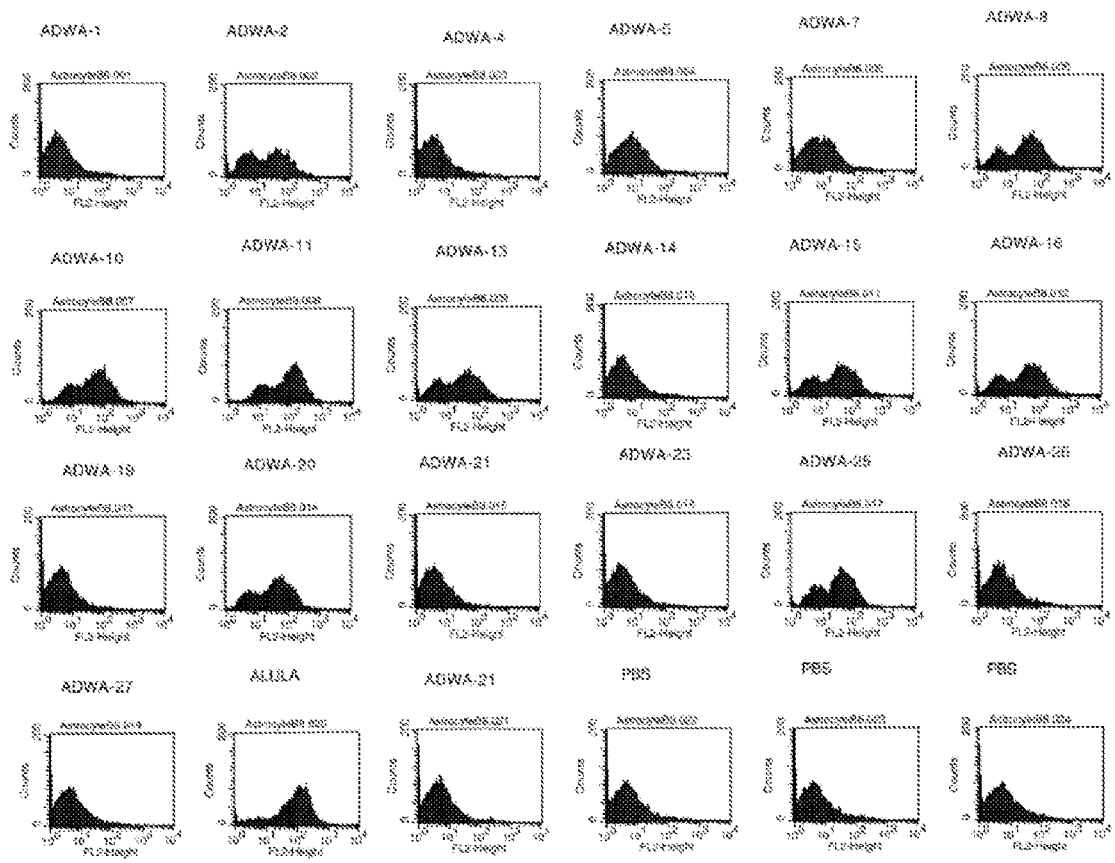
FIG. 1 provides flow cytometry plots of primary astrocytes bound by antibodies as described in Example 1.

Various antibodies that bind to human integrin β8 and that inhibit adhesion of latency associated peptide (LAP) are provided.

II. Definitions

An "antagonist" refers to an agent that binds to an integrin (e.g., αvβ8) and partially or totally blocks stimulation, decreases, prevents, delays activation, inactivates, desensitizes, or down regulates the activity of the integrin.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." The present invention provides for, e.g., antibodies having polynucleotide or polypeptide sequences that have at least 80% identity, e.g., 85%, 90%, 91%, 92%, 93, 94%, 95%, 96%, 97%, 98%, 99%, or 100% identity, to a reference sequence, e.g., CDRs or variable regions of any of antibodies ADWA-2, ADWA-8, ADWA-10, ADWA-11, ADWA-13, ADWA-15, ADWA-16, ADWA-25, and ADWA-20. As described below, the preferred algorithms can account for gaps and the like. Preferably, identity exists over a region that is at least about 25 amino acids or nucleotides in length, or more preferably over a region that is 50-100 or more amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. The terms encompass to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An antibody as described herein can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In some embodiments, the antibody is IgG (e.g., IgG1, IgG2, IgG3, IgG4), IgM, IgA, IgD, or IgE.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

In an antibody, substitution variants have at least one amino acid residue removed and a different residue inserted in its place. The sites of greatest interest for substitutional mutagenesis include the hypervariable regions, but framework alterations are also contemplated. Examples of conservative substitutions are described above.

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution that can be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical (e.g., involved in disulfide bond formation). Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids. For the purposes of this inventor, antibodies are employed in a form that can activate EphA3 present on the surface of myeloproliferative cells or that can kill myeloproliferative cells by ADCC. Thus, in some embodiments an antibody is dimeric. In other embodiments, the antibody may be in a monomeric form that has an active isotype. In some embodiments the antibody is in a multivalent form, e.g., a trivalent or tetravalent form, that can cross-link EphA3.

As used herein, "V-region" refers to an antibody variable region domain comprising the segments of Framework (FW) 1, complementarity-determining region (CDR) 1, FW2, CDR2, FW3, CDR3, and Framework 4. The V region for the heavy and light chains is commonly designated $V_H$ and $V_L$, respectively, or with like terms. The V region is included on Fab, F(ab')2, Fv and scFv antibody fragments described herein, and involved in specific antigen recognition.

As used herein, "complementarity-determining region (CDR)" refers to the three hypervariable regions in each chain that interrupt the four "framework (FW)" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., Nature 321:522-525; 1986; Riechmann et al., Nature 332:323-327, 1988; Verhoeyen et al., Science 239:1534-1536, 1988); Presta, Curr. Op. Struct. Biol. 2:593-596, 1992; U.S. Pat. No. 4,816,567), including techniques such as "superhumanizing" antibodies (Tan et al., J. Immunol. 169: 1119, 2002) and "resurfacing" (e.g., Staelens et al., Mol. Immunol. 43: 1243, 2006; and Roguska et al., Proc. Natl. Acad. Sci USA 91: 969, 1994).

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope).

The same is true for other types of target molecules that form three-dimensional structures. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

A "label" or a "detectable moiety" is a diagnostic agent or component detectable by spectroscopic, radiological, photochemical, biochemical, immunochemical, chemical, or other physical means. Exemplary labels include radiolabels (e.g., $^{111}$In, $^{99m}$Tc, $^{131}$I, $^{67}$Ga) and other FDA-approved imaging agents. Additional labels include $^{32}$P, fluorescent dyes, electron-dense reagents, enzymes, biotin, digoxigenin, or haptens and proteins or other entities which can be made detectable, e.g., by incorporating a radiolabel into the targeting agent. Any method known in the art for conjugating a nucleic acid or nanocarrier to the label may be employed, e.g., using methods described in Hermanson, *Bioconjugate Techniques* 1996, Academic Press, Inc., San Diego.

A "labeled" or "tagged" antibody or agent is one that is bound, either covalently, through a linker or a chemical bond, or noncovalently, through ionic, van der Waals, electrostatic, or hydrogen bonds to a label such that the presence of the antibody or agent may be detected by detecting the presence of the label bound to the antibody or agent.

Techniques for conjugating detectable and therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody will typically bind the primary antibody with at least a 2-fold greater affinity than a non-primary antibody target (e.g., an antibody from a different species or of a different isotype, or a non-antibody target). Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "binds" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value or a range gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "therapeutically effective dose," "effective dose," or "therapeutically effective amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Remington: *The Science and Practice of Pharmacy*, 20th Edition, Gennaro, Editor (2003), and Pickar, *Dosage Calculations* (1999)). For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

The term "pharmaceutically acceptable salts" or "pharmaceutically acceptable carrier" is meant to include salts of the active compounds which are prepared with relatively nontoxic acids or bases, depending on the particular substituents found on the antibodies described herein. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The term "reduce," "reducing," or "reduction," when used in the context of αvβ8-mediate TGFβ activation refers to any detectable negative change or decrease in quantity of a parameter that reflects TGFβ activation, compared to a standard value obtained under the same conditions but in the absence of an antibody as described herein (e.g., anti-αvβ8 antibodies). The level of this decrease following exposure to an antibody as described herein (e.g., anti-αvβ8 antagonists, anti-αvβ8 antibodies and immunoconjugates) is, in some embodiments, at least 10%, 20%, 30%, 40%, 50%, 60%, 70%, 80%, 90%, 95%, or 100%.

The term "compete", as used herein with regard to an antibody, means that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, *Antibodies, A Laboratory Manual*, Cold Spring Harbor Press (1988)); solid phase direct label RIA using I-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

III. Antibodies that Bind Integrin β8

Antibodies (including antibody fragments) that specifically bind to human integrin β8 are provided, as well as methods for treating or preventing diseases for which decrease of TGFβ activation has an ameliorative effect. "Integrin β8" is used interchangeably with β8 and beta-8. The human integrin β8 protein sequence can be found at Uniprot accession number P26012, while the murine integrin β8 sequence has Uniprot accession number QOVBD0. See, also, Moyle et al. *Journal of Biological Chemistry* 266:19650-19658 (1991); Nishimura et al., *J. Biological Chemistry* 269:28708-28715 (1994).

Figure 2:
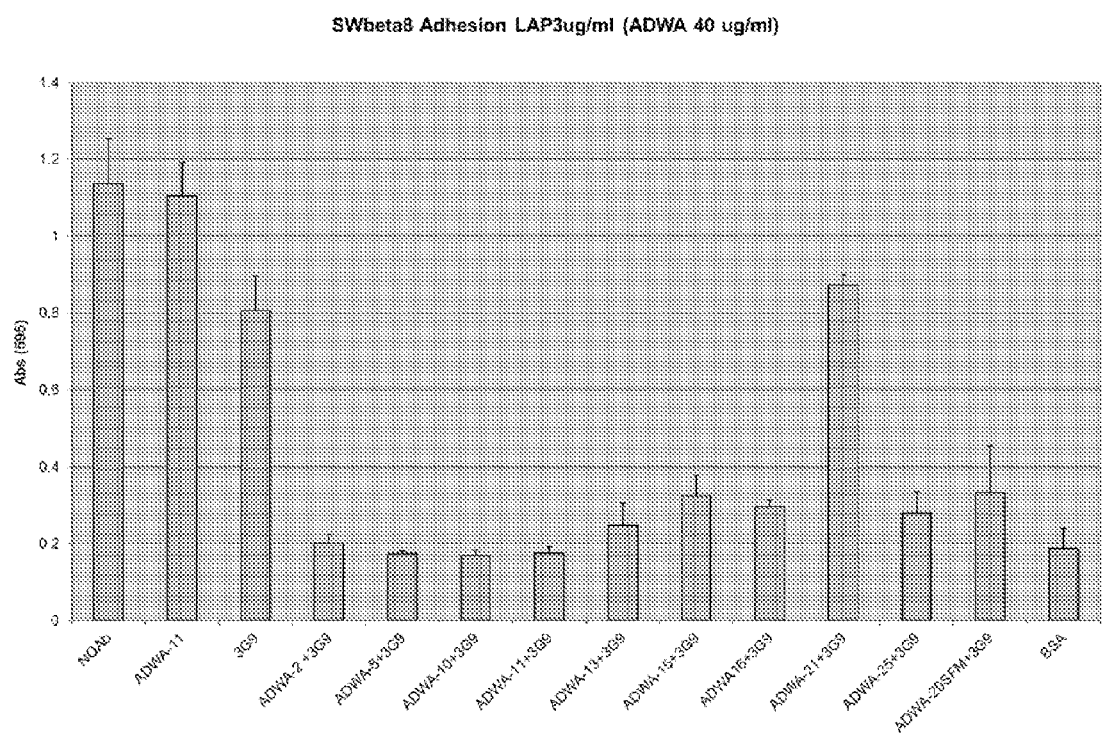
FIG. 2 shows data from LAP adhesion blocking experiments as described in Example 1.

In some embodiments, an antibody that specifically binds to human integrin β8 and inhibits (partially or completely blocks) binding of latency associated peptide (LAP) to αvβ8 is provided. LAP is a ligand for αvβ8. See, e.g., Sheppard, *Cancer and Metastasis Reviews* 24(3):395-402 (2005); Lu et al. *J Cell Sci* 115:4641-4648 (2002). As shown in FIG. 2, antibodies described in the Example inhibit biding of LAP to αvβ8. Antibodies can antagonize LAP binding to αvβ8 with an $IC_{50}$ of, for example, less than e.g., 10, 5, 1, 0.1 nM or lower.

In some embodiments, an antibody of the invention specifically binds to mouse as well as human integrin β8. Each of antibodies ADWA-2, ADWA-8, ADWA-10, ADWA-11, ADWA-13, ADWA-15, ADWA-16, ADWA-25, and ADWA-20 bind to both human and mouse β8. One advantage of such antibodies is that clinical data can be generated for these antibodies in mice as well as humans.

One aspect of blockage of LAP binding to αvβ8 in a cell can be that the antibodies prevent or reduce TGFβ activate in the cell. Thus, in some embodiments, the antibodies described herein are useful for decreasing TGFβ activation in a cell or an animal (e.g., a mouse, human, or other animal).

In some embodiments, the antibodies compete with one of more antibodies selected from ADWA-2, ADWA-8, ADWA-10, ADWA-11, ADWA-13, ADWA-15, ADWA-16, ADWA-25, and ADWA-20. In some embodiments, the antibodies bind to the same epitope as bound by ADWA-2, ADWA-8, ADWA-10, ADWA-11, ADWA-13, ADWA-15, ADWA-16, ADWA-25, and ADWA-20. Monoclonal antibodies, and chimeric, and especially humanized antibodies, are of particular use for human therapeutic uses of the antibodies described herein. Thus, in some embodiments, a αvβ8-specific antibody as described herein comprises the complementarity determining regions (CDRs) of the heavy chain variable region and the light chain variable region of an antibody selected from ADWA-2, ADWA-8, ADWA-10, ADWA-11, ADWA-13, ADWA-15, ADWA-16, ADWA-25, and ADWA-20. For example, the antibody can have CDR1, CDR2, and CDR3 of the heavy chain variable region and CDR1, CDR2, and CDR3 of the light chain variable region of an antibody selected from ADWA-2, ADWA-8, ADWA-10, ADWA-11, ADWA-13, ADWA-15, ADWA-16, ADWA-25, and ADWA-20 and have a heterologous (e.g., human or human-like) framework region.

In some embodiments, the αvβ8-specific antibodies as described herein comprise the complementarity determining regions (CDRs) of the heavy chain variable region sequence and the light chain variable region sequence selected from:
SEQ ID NO:1 and SEQ ID NO:16, respectively;
SEQ ID NO:2 and SEQ ID NO:16, respectively;
SEQ ID NO:3 and SEQ ID NO:16, respectively;
SEQ ID NO:4 and SEQ ID NO:16, respectively;
SEQ ID NO:5 and SEQ ID NO:16, respectively;
SEQ ID NO:6 and SEQ ID NO:16, respectively;
SEQ ID NO:7 and SEQ ID NO:17, respectively;
SEQ ID NO:8 and SEQ ID NO:18, respectively;
SEQ ID NO:9 and SEQ ID NO:19, respectively;
SEQ ID NO:10 and SEQ ID NO:20, respectively;
SEQ ID NO:11 and SEQ ID NO:20, respectively;
SEQ ID NO:12 and SEQ ID NO:20, respectively;
SEQ ID NO:13 and SEQ ID NO:20, respectively;
SEQ ID NO:14 and SEQ ID NO:21, respectively; and
SEQ ID NO:15 and SEQ ID NO:22, respectively.

In some embodiments, the αvβ8-specific antibodies as described herein comprise the heavy chain variable region sequence and the light chain variable region sequence of selected from:
SEQ ID NO:1 and SEQ ID NO:16, respectively;
SEQ ID NO:2 and SEQ ID NO:16, respectively;
SEQ ID NO:3 and SEQ ID NO:16, respectively;
SEQ ID NO:4 and SEQ ID NO:16, respectively;
SEQ ID NO:5 and SEQ ID NO:16, respectively;
SEQ ID NO:6 and SEQ ID NO:16, respectively;
SEQ ID NO:7 and SEQ ID NO:17, respectively;
SEQ ID NO:8 and SEQ ID NO:18, respectively;
SEQ ID NO:9 and SEQ ID NO:19, respectively;
SEQ ID NO:10 and SEQ ID NO:20, respectively;
SEQ ID NO:11 and SEQ ID NO:20, respectively;
SEQ ID NO:12 and SEQ ID NO:20, respectively;
SEQ ID NO:13 and SEQ ID NO:20, respectively;
SEQ ID NO:14 and SEQ ID NO:21, respectively; and
SEQ ID NO:15 and SEQ ID NO:22, respectively.

In some embodiments, the antibody has the heavy chain CDR sequences and light chain CDR sequences found in SEQ ID NO:1 and SEQ ID NO:16, respectively. In some embodiments, the antibody has the heavy chain CDR sequences and light chain CDR sequences found in SEQ ID NO:4 and SEQ ID NO:16, respectively. In some embodiments, the antibody has the heavy chain CDR sequences and light chain CDR sequences found in SEQ ID NO:7 and SEQ ID NO:17, respectively. In some embodiments, the antibody has the heavy chain CDR sequences and light chain CDR sequences found in SEQ ID NO:8 and SEQ ID NO:18, respectively. In some embodiments, the antibody has the heavy chain CDR sequences and light chain CDR sequences found in SEQ ID NO:9 and SEQ ID NO:19, respectively.

Monoclonal antibodies can be obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies can be collected and titered against a β8 ligand (e.g., LAP) in an immunoassay, for example, a solid phase immunoassay with the ligand immobilized on a solid support. In some embodiments, monoclonal antibodies will bind with a $K_d$ of at least about 0.1 mM, e.g., at least about 1 µM, e.g., at least about 0.1 µM or better, e.g., 0.01 µM or lower.

In an exemplary embodiment, an animal, such as a rabbit or mouse is immunized with a β8 polypeptide, or an nucleic acid construct encoding such a polypeptide. The antibodies produced as a result of the immunization can be isolated using standard methods. In some embodiments, the animal is a knockout of integrin β8 and is immunized with a human β8 integrin polypeptide or a fragment thereof.

The immunoglobulins, including binding fragments and other derivatives thereof, of the present invention may be produced readily by a variety of recombinant DNA techniques, including by expression in transfected cells (e.g., immortalized eukaryotic cells, such as myeloma or hybridoma cells) or in mice, rats, rabbits, or other vertebrate capable of producing antibodies by well-known methods. Suitable source cells for the DNA sequences and host cells for immunoglobulin expression and secretion can be obtained from a number of sources, such as the American Type Culture Collection (Catalogue of Cell Lines and Hybridomas, Fifth edition (1985) Rockville, Md.).

In some embodiments, the antibody is a humanized antibody, i.e., an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *PNAS* USA, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994). Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321:522; and Verhoyen et al. (1988) *Science* 239:1534. Humanized antibodies are further described in, e.g., Winter and Milstein (1991) *Nature* 349:293. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well-known procedures from a variety of human cells. The CDRs for producing the immunoglobulins of the present invention will be similarly derived from monoclonal antibodies capable of specifically binding to αvβ8 integrin (e.g., ADWA-2, ADWA-8, ADWA-10, ADWA-11, ADWA-13, ADWA-15, ADWA-16, ADWA-25, and ADWA-20 or antibodies that compete with ADWA-2, ADWA-8, ADWA-10, ADWA-11, ADWA-13, ADWA-15, ADWA-16, ADWA-25, and ADWA-20 for specific binding to αvβ8 integrin).

In some cases, transfer of a CDR to a human framework leads to a loss of specificity for the humanized antibody. In these cases, back mutation can be introduced into the framework regions of the human portion of the antibody. Methods of making back mutations are well known in the art and are described in, e.g., Co et al., *PNAS USA* 88; 2269-2273 (1991) and WO 90/07861.

In some embodiments, the antibodies are antibody fragments such as Fab, F(ab')2, Fv or scFv. The antibody fragments can be generated using any means known in the art including, chemical digestion (e.g., papain or pepsin) and recombinant methods. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)). The antibodies can be expressed in a variety of host cells, including *E. coli*, other bacterial hosts, yeast, and various higher eukaryotic cells such as the COS, CHO, and HeLa cells lines and myeloma cell lines.

Competitive binding assays can be used to identify antibodies that compete with an antibody described herein for specific binding to αvβ8 integrin. Any of a number of competitive binding assays known in the art can be used to measure competition between two antibodies to the same antigen. Briefly, the ability of different antibodies to inhibit the binding of another antibody is tested. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pairwise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

IV. Therapeutic Treatment

As discussed above, the antibodies (including antibody fragments) described herein can be used to reduce TGFβ activation in a cell or an animal. Accordingly, the antibodies can be administered to an animal (e.g., a human or non-human animal) in need thereof, thereby reducing TGFβ activation in the animal. Diseases for which reduction of TGFβ is at least ameliorative include, but are not limited to, asthma, multiple sclerosis, acute lung injury, rheumatoid arthritis, psoriasis and chronic obstructive pulmonary disease. For example, the inventors have found that β8 knockout mice have ameliorated symptoms in asthma, multiple sclerosis, and acute lung injury mouse models compared to those mouse models expressing native integrin β8.

Accordingly, compositions, including pharmaceutical compositions, comprising one or more antibody described herein are provided. For example, a pharmaceutical composition comprising a humanized ADWA-2, ADWA-8, ADWA-10, ADWA-11, ADWA-13, ADWA-15, ADWA-16, ADWA-25, or ADWA-20 antibody is provided.

In some embodiments, the pharmaceutical composition comprises an antibody or antibody fragment comprising the heavy chain CDR sequences (CDR1, CDR2, and CDR3) and light chain CDR sequences (CDR1, CDR2, and CDR3) selected from the group consisting of:

SEQ ID NO:1 and SEQ ID NO:16, respectively;
SEQ ID NO:2 and SEQ ID NO:16, respectively;
SEQ ID NO:3 and SEQ ID NO:16, respectively;
SEQ ID NO:4 and SEQ ID NO:16, respectively;
SEQ ID NO:5 and SEQ ID NO:16, respectively;
SEQ ID NO:6 and SEQ ID NO:16, respectively;
SEQ ID NO:7 and SEQ ID NO:17, respectively;
SEQ ID NO:8 and SEQ ID NO:18, respectively;
SEQ ID NO:9 and SEQ ID NO:19, respectively;
SEQ ID NO:10 and SEQ ID NO:20, respectively;
SEQ ID NO:11 and SEQ ID NO:20, respectively;
SEQ ID NO:12 and SEQ ID NO:20, respectively;
SEQ ID NO:13 and SEQ ID NO:20, respectively;
SEQ ID NO:14 and SEQ ID NO:21, respectively; and
SEQ ID NO:15 and SEQ ID NO:22, respectively.

In some embodiments, the antibody has the heavy chain CDR sequences and light chain CDR sequences found in SEQ ID NO:1 and SEQ ID NO:16, respectively. In some embodiments, the antibody has the heavy chain CDR sequences and light chain CDR sequences found in SEQ ID NO:4 and SEQ ID NO:16, respectively. In some embodiments, the antibody has the heavy chain CDR sequences and light chain CDR sequences found in SEQ ID NO:7 and SEQ ID NO:17, respectively. In some embodiments, the antibody has the heavy chain CDR sequences and light chain CDR sequences found in SEQ ID NO:8 and SEQ ID NO:18, respectively. In some embodiments, the antibody has the heavy chain CDR sequences and light chain CDR sequences found in SEQ ID NO:9 and SEQ ID NO:19, respectively.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

The compositions of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

Formulations suitable for oral administration can comprise: (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the PE. The size of the dose also will be determined by the existence, nature, and extent of any adverse side-effects that accompany the administration of a particular compound or vector in a particular subject.

In determining the effective amount of the antagonists of αvβ8 integrin to be administered a physician may evaluate circulating plasma levels of the antagonist and antagonist toxicity. In general, the dose equivalent of an antagonist is from about 1 ng/kg to 10 mg/kg for a typical subject.

For administration, the antagonists of αvβ8 integrin can be administered at a rate determined by the $LD_{50}$ of the antagonist, and the side-effects of the antagonist at various concentrations, as applied to the mass and overall health of the subject. Administration can be accomplished via single or divided doses.

The compositions may be administered on a regular basis (e.g., daily) for a period of time (e.g., 2, 3, 4, 5, 6, days or 1-3 weeks or more). The compositions can be administered directly to the mammalian subject to reduce TGFβ activation using any route known in the art, including e.g., by injection (e.g., intravenous, intraperitoneal, subcutaneous, intramuscular, or intradermal), inhalation, transdermal application, rectal administration, or oral administration.

EXAMPLES

Example 1

Nine antibodies (designated ADWA-2, ADWA-8, ADWA-10, ADWA-11, ADWA-13, ADWA-15, ADWA-16, ADWA-20, and ADWA-25) were identified that block adhesion to TGFβ1 LAP, cross react with murine β8 (as determined with flow cytometry on murine astrocytes) and block TGFβ activation (as determined with β83.7.12-serial dilutions in a co-culture bioassay with mink lung epithelial cells). The most potent antibody, ADWA11, appears to have an IC50 for inhibiting TGFβ activation of less than 5 nM (based on nearly complete inhibition by a concentration of antibody of 1 microgram/ml (~6.3 nM)).

Figure 3:
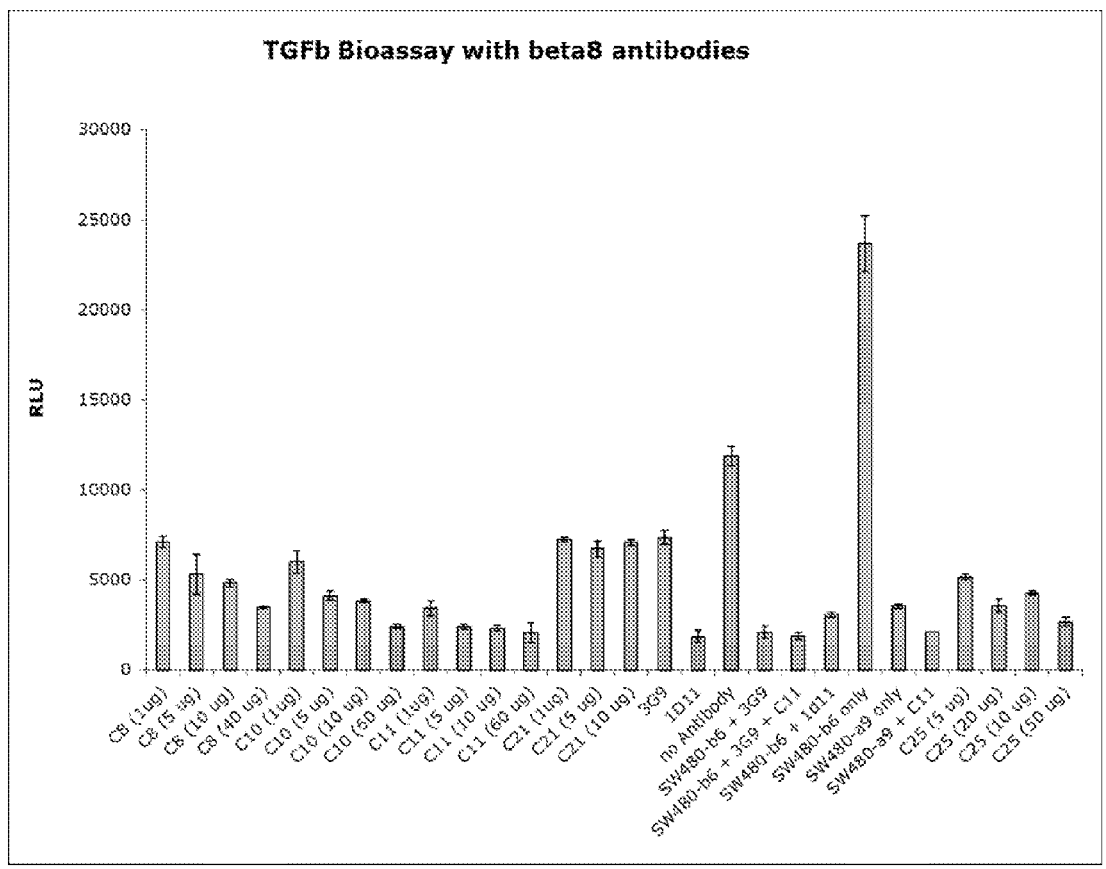
FIG. 3 shows data for TGFβ activation as described in Example 1.
Figure 4:
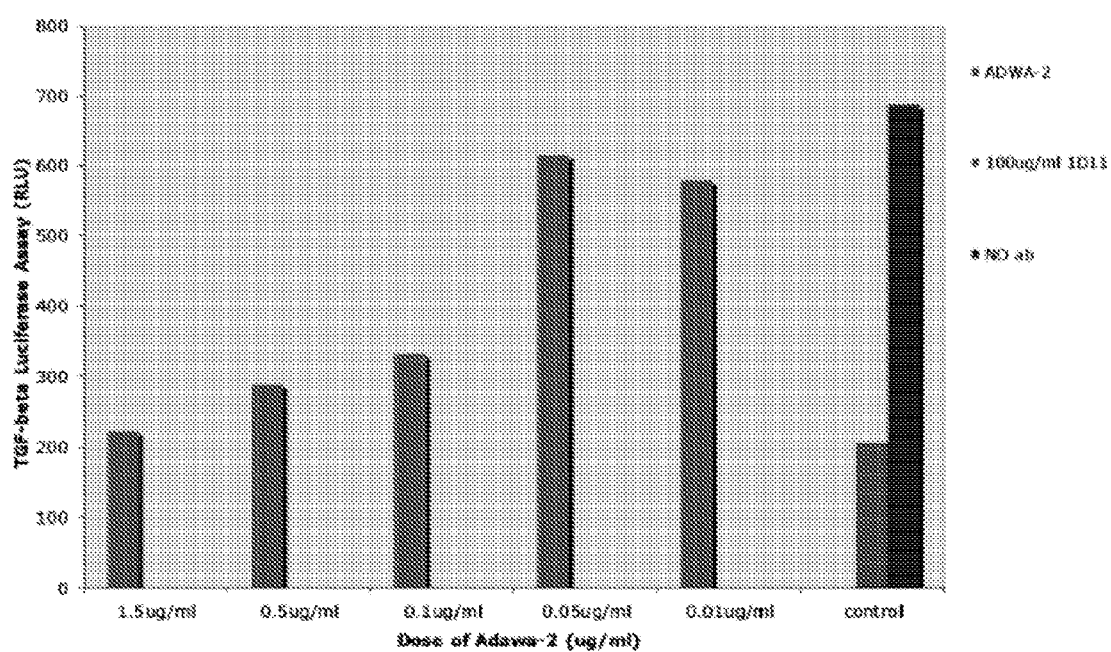
FIG. 4 shows data for ADWA-2 blocking of TGFβ activation at the indicated concentrations. Controls shown on the right include the 1D11 antibody specific for TGFβ, and no antibody.
Figure 5:
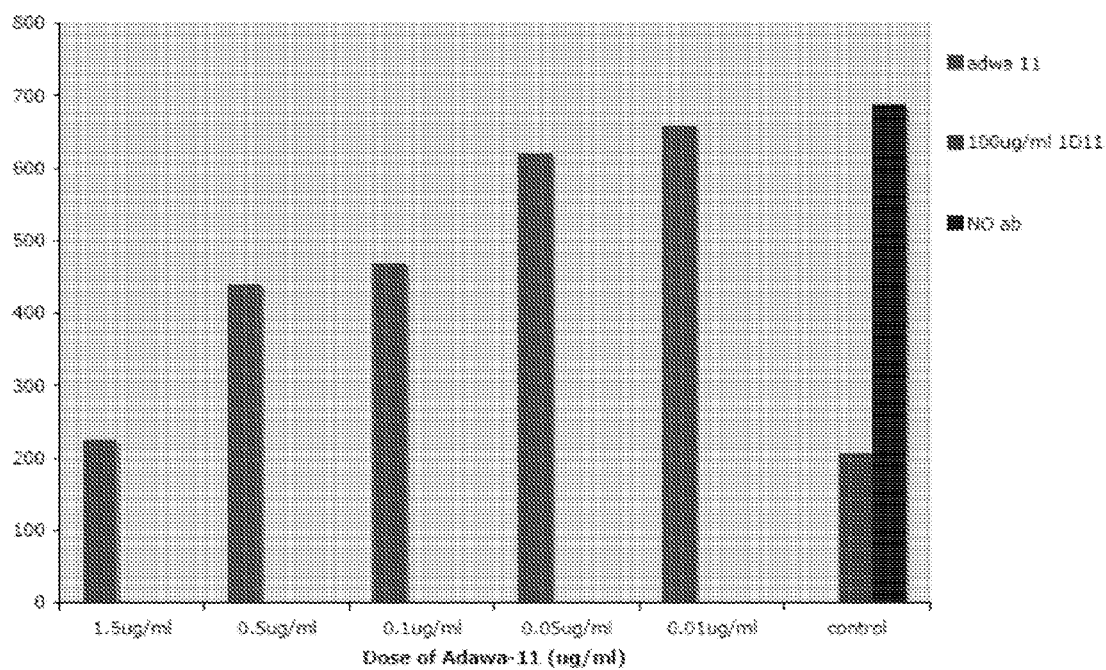
FIG. 5 shows data for ADWA-11 blocking of TGFβ activation at the indicated concentrations. Controls shown on the right include the 1D11 antibody specific for TGFβ, and no antibody.
Figure 6:
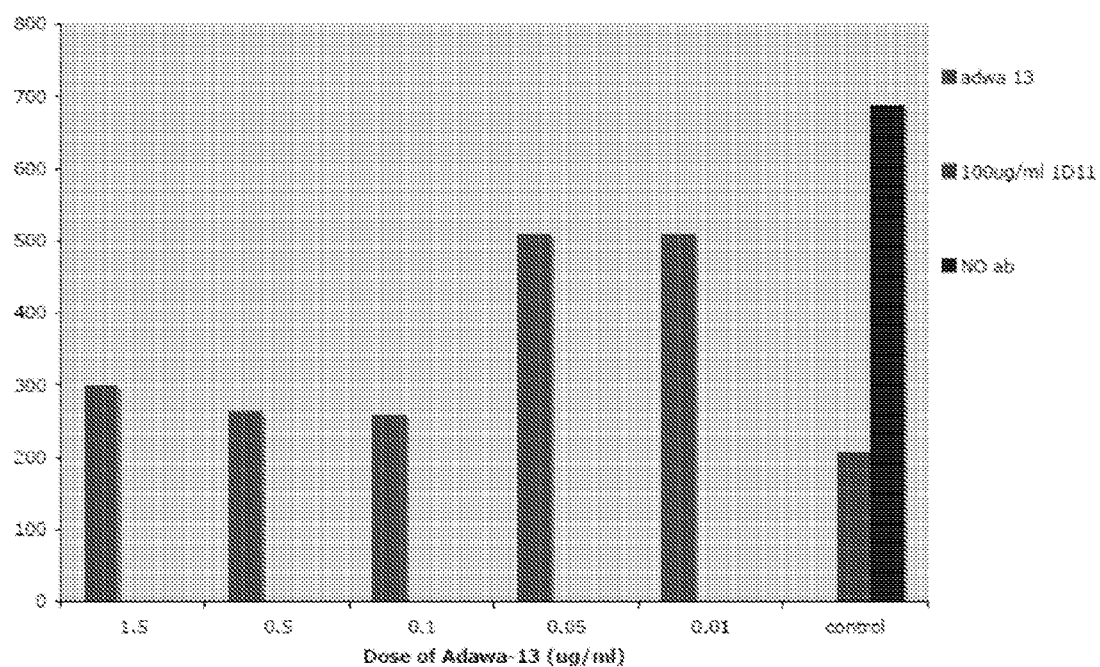
FIG. 6 shows data for ADWA-13 blocking of TGFβ activation at the indicated concentrations. Controls shown on the right include the 1D11 antibody specific for TGFβ, and no antibody.
Figure 7:
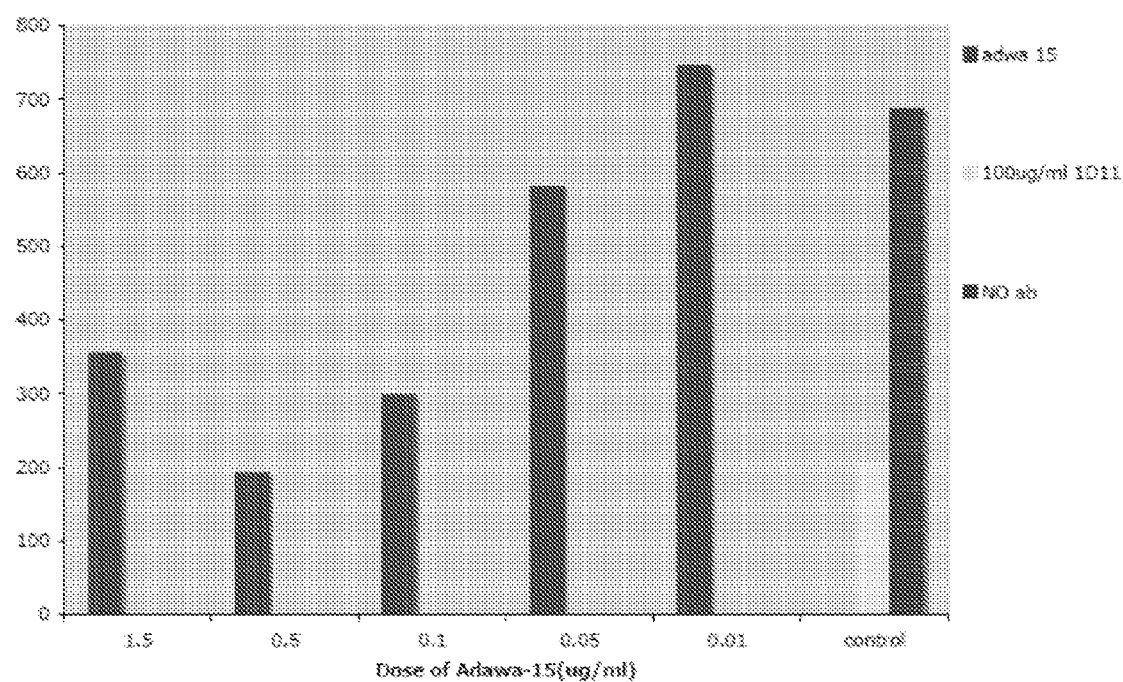
FIG. 7 shows data for ADWA-15 blocking of TGFβ activation at the indicated concentrations. Controls shown on the right include the 1D11 antibody specific for TGFβ, and no antibody.
Figure 8:
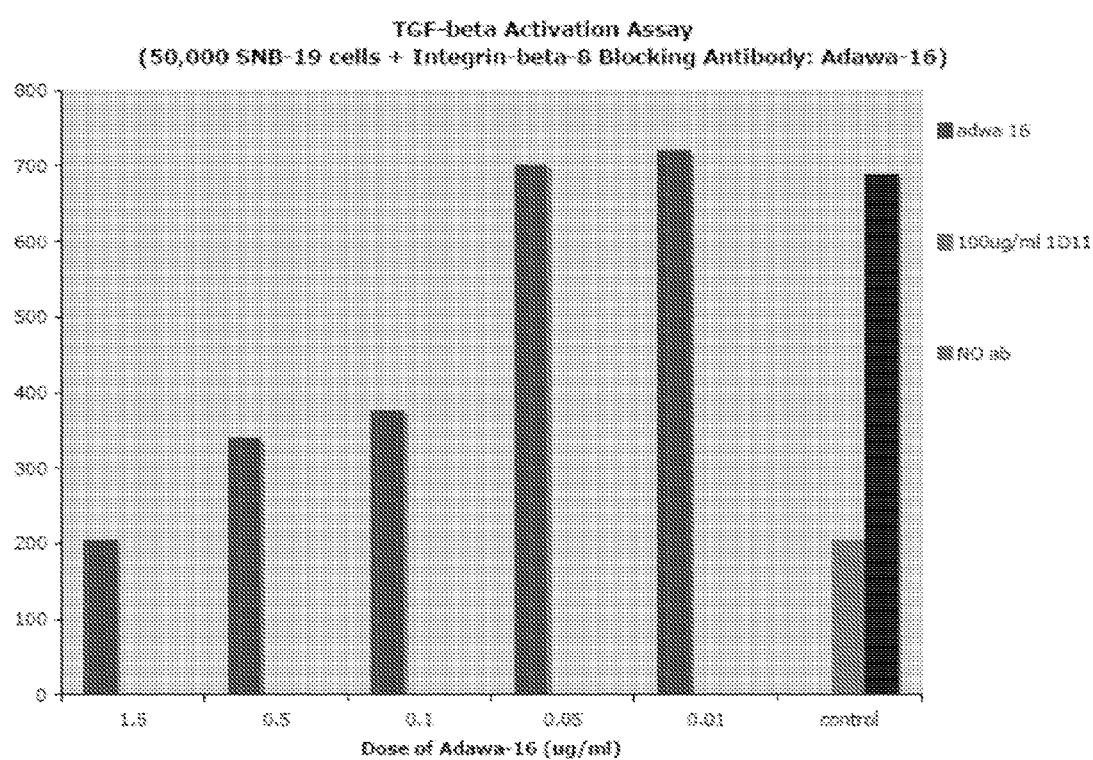
FIG. 8 shows data for ADWA-16 blocking of TGFβ activation at the indicated concentrations. Controls shown on the right include the 1D11 antibody specific for TGFβ, and no antibody.
Figure 9:
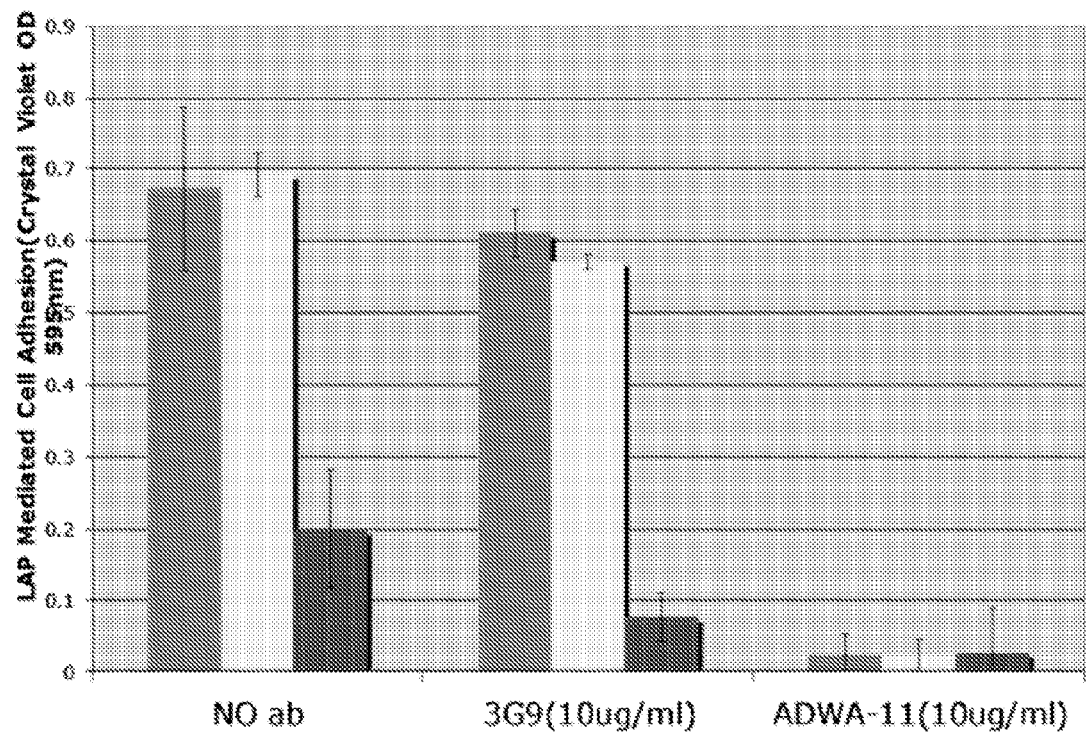
FIG. 9 shows data for ADWA-11 blocking of LAP adhesion. LAP concentrations for each sample are, from left to right, 3 ug/ml, 1 ug/ml, and 0.3 ug/ml. Controls are no antibody (left) and 3G9 antibody specific for 06 (middle).
Figure 10:
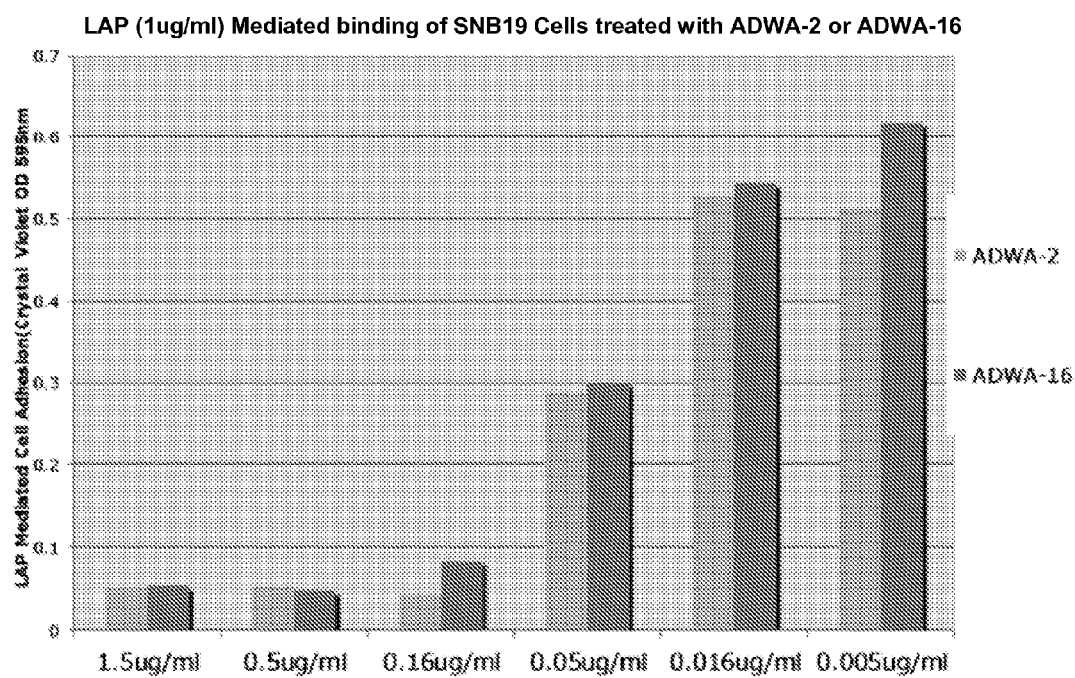
FIG. 10 shows data for ADWA-2 (left) and ADWA-16 (right) blocking of LAP adhesion at the indicated concentrations. LAP was contacted with cells at 1 ug/ml.
Figure 11:
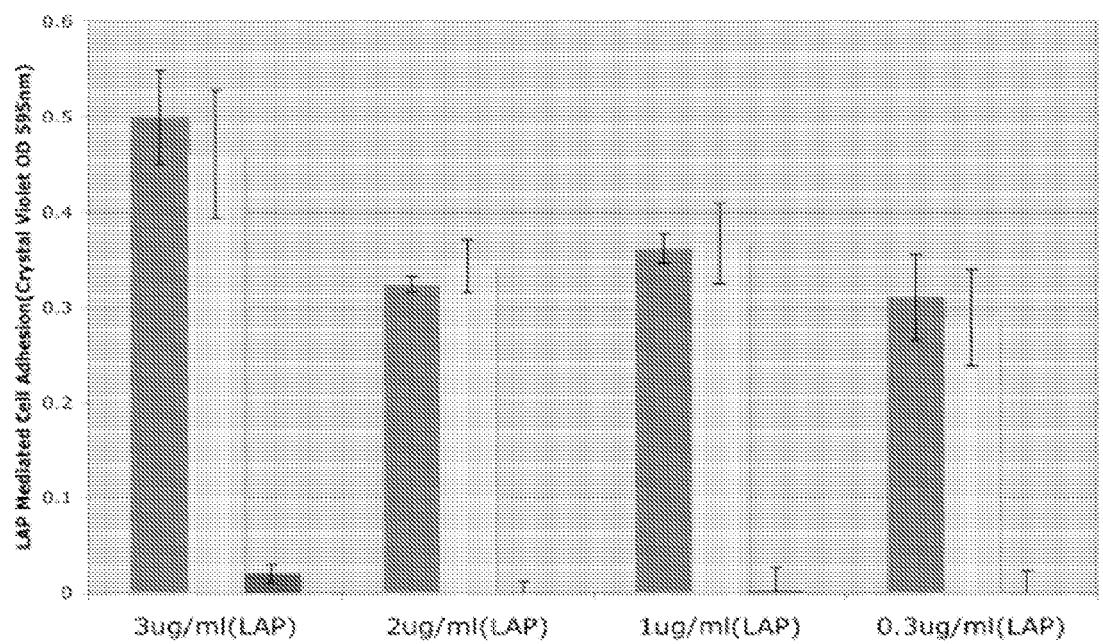
FIG. 11 shows data for ADWA-11 blocking of LAP adhesion. LAP concentrations for each sample are shown. Controls are no antibody (left) and 3G9 antibody specific for β6 (middle) for each concentration of LAP.
Figure 12:
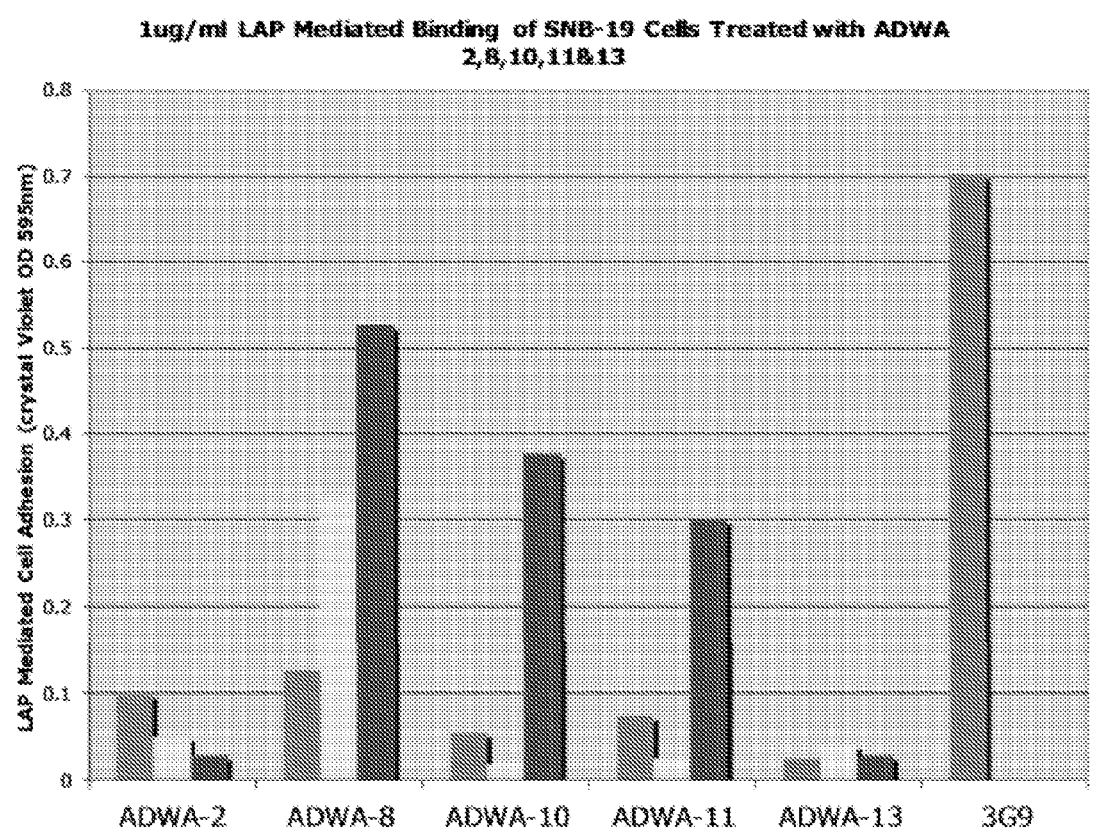
FIG. 12 shows data for ADWA-2, ADWA-8, ADWA-10, ADWA-11, and ADWA-13 blocking of LAP adhesion at various antibody concentrations. LAP was contacted with cells at 1 ug/ml. For each antibody, left to right, concentration was 10 ug/ml, 1 ug/ml, and 0.1 ug/ml. Results for control 3G9 antibody are shown on the right.
Figure 13:
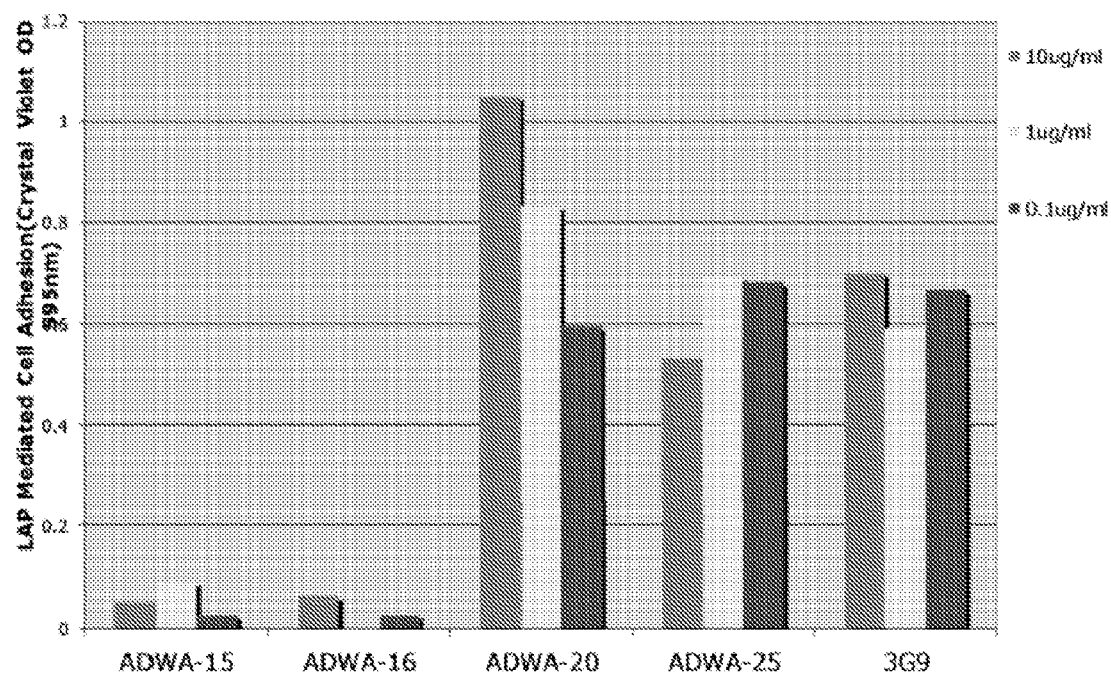
FIG. 13 shows data for ADWA-15, ADWA-16, ADWA-20, and ADWA-25 blocking of LAP adhesion at various antibody concentrations. LAP was contacted with cells at 1 ug/ml. For each antibody, left to right, concentration was 10 ug/ml, 1 ug/ml, and 0.1 ug/ml. Results for control 3G9 antibody are shown on the right.

The antibodies were made by immunizing rare β8 knockout mice that survive into young adulthood with purified human αvβ8. Flow cytometry plots are with primary murine astrocytes and show that ADWA-2, ADWA-8, ADWA-10, ADWA-11, ADWA-13, ADWA-15, ADWA-16, ADWA-20, and ADWA-25 all recognize the mouse integrin, whereas several others do not. See, FIG. 1. The same antibodies block adhesion of 08 transfected SW480 cells to LAP and TGFβ activation by the same cells. See, FIGS. 2 and 3, respectively. Because the cells used also expressed the αvβ6 integrin, the results for these assays also include the β6 blocking antibody, 3G9.

Additional TGFβ activation studies were carried out with individual antibodies to determine their ability to block activation of β8-transfected SNB-19 cells at various concentrations. The results are shown in FIGS. 4-8 for ADWA-2, ADWA-11, ADWA-13, ADWA-15, and ADWA-16. Additional LAP blocking assays were also carried out in β8-transfected SNB-19 cells. Results are shown in FIGS. 9-13.

The results show that ADWA-2, ADWA-16, ADWA-15, ADWA-11, ADWA-13, and ADWA-10 are more effective for blocking LAP adhesion and inhibiting TGFβ activation.

Example 2

In order to further characterize the sequences of the ADWA-2, ADWA-8, ADWA-10, ADWA-11, ADWA-13, ADWA-15, ADWA-16, ADWA-20, and ADWA-25 antibodies, total RNA was harvested from the hybridoma cell line expressing each antibody. RNA was isolated using Qiagen® RNeasy® kit and QIAshredder. Reverse transcriptase PCR was carried out using oligo dT and Clonetech® SMART™ IIa oligo. PCR was carried out using SMART-sense oligo and mouse IgG1 or kappa constant domain oligos.

Each of the 500 bp PCR products (from each antibody clone) was separated using gel electrophoresis, and cloned into Invitrogen™ Zero Blunt® TOPO® cloning kit, and transformed into cells. For each antibody hybridoma clone, 16 colonies were selected (288 total colonies).

The cloned DNA was sequenced by rolling circle amplification (RCA), and analyzed with Invitrogen™ AlignX® and TIBCO® Spotfire®. The CDR and V-region sequences were initially analyzed to determine variability within each antibody clone, and then compared between clones.

Nearly all of the VH sequences of ADWA16 and ADWA2 were identical (SEQ ID NO:1), with 2 variants found in the 16 ADWA2 samples (SEQ ID NOs:2 and 3). The primary ADWA13 sequence is shown in SEQ ID NO:4, with 2 variants shown in SEQ ID NOs:5 and 6. The VH sequences of these three antibodies was quite similar, with 2 amino acid changes in CDR2 (positions 60 and 66) and 3 in the FW regions (positions 19, 45, and 78).

The VH sequences for ADWA10, ADWA11, ADWA15, ADWA20, and ADWA25 were identical within each clone, but distinct from other clones. The VH sequences are shown in SEQ ID NOs: 7 (ADWA15), 8 (ADWA11), 9 (ADWA10), 14 (ADWA20), and 15 (ADWA25). Three VH sequence variants were found among the 16 ADWA8 samples (SEQ ID NOs:11-13), with the primary sequence shown as SEQ ID NO:10.

As for light chains, ADWA2, ADWA13, and ADWA16 were found to share the same Vkappa sequence (SEQ ID NO:16). The Vkappa sequences for ADWA15, ADWA11, and ADWA10 are shown as SEQ ID NOs:17, 18, and 19, respectively. The Vkappa sequences for ADWA8, ADWA20, and ADWA25 are shown as SEQ ID NOs:20, 21, and 22, respectively.

The antibody sequences were confirmed and are shown in Table 1 below. Table 1 shows the sequences for the heavy chain variable ($V_H$) region, light chain variable ($V_L$) region, heavy chain CDRs (HCDR), light chain CDRs (LCDR), $V_H$-encoding nucleotides, and $V_L$-encoding nucleotides. CDRs are shown according to both Chothia (underlined) and Kabat (bold) designations.

TABLE 1

| SEQ ID NO: | Description | Sequence |
|---|---|---|
| | | $V_H$ SEQUENCES-AMINO ACIDS |
| 1 | ADWA2 ADWA16 | QVQLQQSGAELAKPGASMKMSCKASGYTFS<u>SYWI</u>YWVKQRPGQGLEWIG<u>YIN PTTGYTEYNQKFRD</u>KATLTADKSSNTAYMQLSSLTSEDSAVYYCATEGGNWE DYWGQGTTLTVSS |
| 2 | ADWA2-1 | QVQLQQSGAELAKPGASMKMSCKAS<u>GYTFS</u>SYWIYWVKQRPGQGLEWIG<u>YIN PTTGYTEYNQKFRD</u>KVTLTADKSSNTAYMQLSSLTSEDSAVYYCATEGGNWE DYWGQGTTLTVSS |
| 3 | ADWA2-2 | QVQLQQSGAELTKPGASMKMSCKAS<u>GYTFS</u>SYWIYWVKQRPGQGLEWIG<u>YIN PTTGYTEYNQKFRD</u>KVTLTADKSSNTAYMQLSSLTSEDSAVYYCATEGGNWE DYWGQGTTLTVSS |
| 4 | ADWA13 | QVQLQQSGAELAKPGASVKMSCKAS<u>GYTFS</u>SYWIYWVKQRPGQVLEWIG<u>YIN PTTGYTDYNQKFKD</u>KATLTADKSSTAYMQLSSLTSEDSAVYYCATEGGNWE DYWGQGTTLTVSS |
| 5 | ADWA13-1 | QVQLQQSGAELAKPGASVKMSCKAS<u>GYTFS</u>SYWIYWVKQRPGQVLEWIG<u>YIN PTTGYTDYNQKFKD</u>KATLTADKSSTAYMQLSSLTSEDSTVYYCATEGGNWE DYWGQGTTLTVSS |
| 6 | ADWA13-2 | QVQLQQSGAELTKPGASVKMSCKAS<u>GYTFS</u>SYWIYWVKQRPGQVLEWIG<u>YIN PTTGYTDYNQKFKD</u>KATLTADKSSTAYMQLSSLTSEDSTVYYCATEGGNWE DYWGQGTTLTVSS |
| 7 | ADWA15 | QVQLQQPGSVLVRPGASVKLSCKAS<u>GYTFT</u>SSWMHWAKQRPGQGLEWIG<u>EIH PNSGNS</u>IYNEKFKDKATLTVDTSSSTAYVDLSSLTSEDSAVYYCARWGDFDY WGQGTSVTVSS |
| 8 | ADWA11 | EVQLQQSGAELVRPGAFVKLSCKAS<u>GFNIK</u>DYYMNWVLQRPEQGLEWIGWID PDNGNTIYDPKFQGKASITADTSSNTAYLQLSSLTSEDTAVYYCARRLLMDY WGQGTSVTVSS |
| 9 | ADWA10 | EVLLQQSGPELVKPGASVKIPCKAS<u>GYTFT</u>NYNMDWVKQSHGKSLEWIG<u>DIN PNSGGSV</u>YNQKFKGKATLTVDKSSSTAYMELRSLTSEDTAVYYCARWAYYGE RFHYFDYWGQGTTLTVSS |
| 10 | ADWA8 | QVQLQQPGSELVRPGASVKLSCKAS<u>GYTFT</u>SYWMHWVKQRPGQGLEWIG<u>NIY PGSGRT</u>NYDEKFKSKATLTVDTSSSTAYMQLSSLTSEDSAVYYCTRPLQYRY DVYPMDYWGQGTSVTVSS |
| 11 | ADWA8-1 | QVQLQQPGSELVRPGASVKLSCKAS<u>GYTFT</u>SYWMHWVKQRPGQGLEWIG<u>NIY PGSGRT</u>NYDEKFRSKATLTVDTSSSTAYMQLSSLTSEDSAVYYCTRPLQYRY DVYPMDYWGQGTSVTVSS |
| 12 | ADWA8-2 | QVQLQQPGSELVRPGASVKLSCKAS<u>GYTFT</u>SYWMHWVKQPGQGLEWIG<u>NIY PGSGRT</u>NYDEKFKSKATLTVDTSSSTAYMQLTSLTSEDSAVYYCTRPLQYRY DVYPMDYWGQGTSVTVSS |
| 13 | ADWA8-3 | QVQLQQPGSELVRPGASMKLSCKAS<u>GYTFT</u>SYWMHWVKQRPGQGLEWIG<u>NIY PGSGRT</u>NYDEKFKSKATLTVDTSSSTAYMQLTSLTSEDSAVYYCTRPLQYRY DVYPMDYWGQGTSVTVSS |
| 14 | ADWA20 | DVQLQESGPGLVKPSQSLSLTCTVT<u>GYSITS</u>DFAWSWIRQFPGNKLEWMG<u>YI SYSGSTGYNPSLKS</u>RISITRDTSKNQFFLQLNSVTTEDTATYYCTRRGLYHW GFPYWGQGTLVTVSA |
| 15 | ADWA25 | EVQLVESGGDLVKPGGSLKLSCAAS<u>GFTES</u>SYGMSWVRQTPDKRLEWVAT<u>IS GGGSYT</u>YYPDSVKGRFTISRHNAKNTLYLQMSSLKSEDTAMYYCASDPYYYG RRDLAWIAYWGQGTLVTVSA |
| | | $V_L$ SEQUENCES-AMINO ACIDS |
| 16 | ADWA2 ADWA13 ADWA16 | DIQMTQTTSSLSASLGDRVTISCRASQDISNYLNWYQQKPDGTVKLLIYYTS RLYSGVPSRFSGSGSGTDYSLTISNLEPKDIATYYCQQFSELPRTEGGGTKL EIK |
| 17 | ADWA15 | DVQMTQTTSSLSASLGDRVTISCRASQDISNYLNWYQQKPDGTVKLLIYYTS RLHSGVPSRFSGSGSGTDFSLTISNLEPEDIATYYCQQYNKVPLTFGGGTKL ELK |
| 18 | ADWA11 | DIVMTQAAPSVPVTPGESVSISCRSTKSLLHENGNTYLFWFLQRPGQSPQRL IYYMSNLASGVPDRFSGRGSGTDFTLRISRVEAEDVGVYYCMQSLEYPFTFG TGTKLEIK |
| 19 | ADWA10 | QIVLSQSPAILSASPGEKVTMTCRASSSVSYMHWYQQKSGSSPKPWIYATSN LASGVPARFSGSGSGTSYSLTISRVEAEDAATYYCQQWSSNPPTFGGGTKLE IK |
| 20 | ADWA8 | DIQMTQSPASLSASVGETVTITCRASENIDSYLAWYQQKQGKSPQLLVYAAT LLPDGVPSRFSGSGSGTQYSLKINSLQSEDVARYYCQHYYNTPWTFGGGTKL EIK |

TABLE 1 -continued

| SEQ ID NO: | Description | Sequence |
|---|---|---|
| 21 | ADWA20 | DIVMTQSHKFMSTSVGDRVSITCKASQDVSSAVAWYQQKPGQSPKLLIYWAS THRTGVPDRFTGSGSGTDYTLTVSNVQAEDLALYYCQQHYITPYTFGGGTKL EIK |
| 22 | ADWA25 | DIVMTQSQKFMSTSVGDRVSVTCKASQNVGTNVAWYQQKPGQSPKALIYSAS YRYSGVPDRFTGSGSGTDFTLTISNVQSEDLAEYFCQQYNSYPYTEGGGTKL EIK |

V<sub>H</sub> CDR SEQUENCES-AMINO ACIDS

| 23 | ADWA2 ADWA16 ADWA2-1 ADWA2-2 ADWA13 ADWA13-1 ADWA13-2 HCDR1 | <u>GYTFS</u>SYWIY (UNDERLINE = SEQ ID NO: 88; BOLD = SEQ ID NO: 89) |
| 24 | ADWA2 ADWA16 ADWA2-1 ADWA2-2 HCDR2 | YIN<u>PTTGYTE</u>YNQKFRD (UNDERLINE = SEQ ID NO: 90) |
| 25 | ADWA2 ADWA16 ADWA2-1 ADWA2-2 ADWA13 ADWA13-1 ADWA13-2 HCDR3 | EGGNWEDY |
| 26 | ADWA13 ADWA13-1 ADWA13-2 HCDR2 | YINPTTGYTDYNQKFKD (UNDERLINE = SEQ ID NO: 90) |
| 27 | ADWA15 HCDR1 | <u>GYTFTSS</u>WMH (UNDERLINE = SEQ ID NO: 91; BOLD = SEQ ID NO: 92) |
| 28 | ADWA15 HCDR2 | EIHPNSGNSIYNEKFKD (UNDERLINE = SEQ ID NO: 93) |
| 29 | ADWA15 HCDR3 | WGDFDY |
| 30 | ADWA11 HCDR1 | <u>GFNIK</u>DYYMN (UNDERLINE = SEQ ID NO: 94; BOLD = SEQ ID NO: 95) |
| 31 | ADWA11 HCDR2 | WIDPDNGNTIYDPKFQG (UNDERLINE = SEQ ID NO: 96) |
| 32 | ADWA11 HCDR3 | RLLMDY |
| 33 | ADWA10 HCDR1 | <u>GYTFT</u>NYNMD (UNDERLINE = SEQ ID NO: 97; BOLD = SEQ ID NO: 98) |
| 34 | ADWA10 HCDR2 | DINPNSGGSVYNQKFKG (UNDERLINE = SEQ ID NO: 99) |
| 35 | ADWA10 HCDR3 | WAYYGERFHYFDY |
| 36 | ADWA8 ADWA8-1 ADWA8-2 ADWA8-3 HCDR1 | <u>GYTFTS</u>YWMH (UNDERLINE = SEQ ID NO: 100; BOLD = SEQ ID NO: 101) |
| 37 | ADWA8 ADWA8-2 ADWA8-3 HCDR2 | NIYPGSGRTNYDEKFKS (UNDERLINE = SEQ ID NO: 102) |
| 38 | ADWA8 ADWA8-1 ADWA8-2 ADWA8-3 HCDR3 | PLQYRYDVYPMDY |
| 39 | ADWA8-1 HCDR2 | NIYPGSGRTNYDEKFRS (UNDERLINE = SEQ ID NO: 102) |
| 40 | ADWA20 HCDR1 | <u>GYSITS</u>DFAWS (UNDERLINE = SEQ ID NO: 103; BOLD = SEQ ID NO: 104) |
| 41 | ADWA20 HCDR2 | YISYSGSTGYNPSLKS (UNDERLINE = SEQ ID NO: 105) |
| 42 | ADWA20 HCDR3 | RGLYHWGFPY |
| 43 | ADWA25 HCDR1 | <u>GFTFS</u>SYGMS (UNDERLINE = SEQ ID NO: 106; BOLD = SEQ ID NO: 107) |

TABLE 1 -continued

| SEQ ID NO: | Description | Sequence |
|---|---|---|
| 44 | ADWA25 HCDR2 | TISGGGSYTYYPDSVKG |
| 45 | ADWA25 HCDR3 | DPYYYGRRDLAWIAY |

V<sub>L</sub> CDR SEQUENCES-AMINO ACIDS

| SEQ ID NO: | Description | Sequence |
|---|---|---|
| 46 | ADWA2 ADWA13 ADWA16 ADWA15 LCDR1 | RASQDISNYLN |
| 47 | ADWA2 ADWA13 ADWA16 LCDR2 | YTSRLYS |
| 48 | ADWA2 ADWA13 ADWA16 LCDR3 | QQFSELPRT |
| 49 | ADWA15 LCDR2 | YTSRLHS |
| 50 | ADWA15 LCDR3 | QQYNKVPLT |
| 51 | ADWA11 LCDR1 | RSTKSLLHFNGNTYLF |
| 52 | ADWA11 LCDR2 | YMSNLAS |
| 53 | ADWA11 LCDR3 | MQSLEYPFT |
| 54 | ADWA10 LCDR1 | RASSSVSYMH |
| 55 | ADWA10 LCDR2 | ATSNLAS |
| 56 | ADWA10 LCDR3 | QQWSSNPPT |
| 57 | ADWA8 LCDR1 | RASENIDSYLA |
| 58 | ADWA8 LCDR2 | AATLLPD |
| 59 | ADWA8 LCDR3 | QHYYNTPWT |
| 60 | ADWA20 LCDR1 | KASQDVSSAVA |
| 61 | ADWA20 LCDR2 | WASTRHT |
| 62 | ADWA20 LCDR3 | QQHYITPYT |
| 63 | ADWA25 LCDR1 | KASQNVGTNVA |
| 64 | ADWA25 LCDR2 | SASYRYS |
| 65 | ADWA25 LCDR3 | QQYNSYPYT |

V<sub>H</sub> SEQUENCES-NUCLEIC ACIDS

| SEQ ID NO: | Description | Sequence |
|---|---|---|
| 66 | ADWA16-1 | CAGGTCCAGCTTCAGCAGTCTGGGGCTGAACTGGCAAAACCTGGGGCCTCAA<br>TGAAGATGTCCTGCAAGGCTTCTGGCTACACCTTTTCTAGCTACTGGATATA<br>TTGGGTAAAACAGAGGCCTGGACAGGGTCTGGAATGGATTGGATACATTAAT<br>CCTACCACTGGTTATACTGAGTACAATCAGAAGTTCAGGGACAAGGCCACAT<br>TGACTGCAGACAAATCCTCCAACACAGCCTACATGCAACTGAGCAGCCTGAC<br>ATCTGAGGACTCTGCAGTCTATTACTGTGCAACAGAGGGAGGTAATTGGGAG<br>GACTACTGGGGCCAAGGCACCACTCTCACAGTCTCCTCA |
| 67 | ADWA2-1 | CAGGTCCAGCTTCAGCAGTCTGGGGCTGAACTGGCAAAACCTGGGGCCTCAA<br>TGAAGATGTCCTGCAAGGCTTCTGGCTACACCTTTTCTAGCTACTGGATATA<br>TTGGGTAAAACAGAGGCCTGGACAGGGTCTGGAATGGATTGGATACATTAAT<br>CCTACCACTGGTTATACTGAGTACAATCAGAAGTTCAGGGACAAGGTCACAT<br>TGACTGCAGACAAATCCTCCAACACAGCCTACATGCAACTGAGCAGCCTGAC<br>ATCTGAGGACTCTGCAGTCTATTACTGTGCAACAGAGGGAGGTAATTGGGAG<br>GACTACTGGGGCCAAGGCACCACTCTCACAGTCTCCTCA |
| 68 | ADWA2-2 | CAGGTCCAGCTTCAGCAGTCTGGGGCTGAACTGACAAAACCTGGGGCCTCAA<br>TGAAGATGTCCTGCAAGGCTTCTGGCTACACCTTTTCTAGCTACTGGATATA<br>TTGGGTAAAACAGAGGCCTGGACAGGGTCTGGAATGGATTGGATACATTAAT |

TABLE 1-continued

| SEQ ID NO: | Description | Sequence |
|---|---|---|
| | | CCTACCACTGGTTATACTGAGTACAATCAGAAGTTCAGGGACAAGGCCACAT<br>TGACTGCAGACAAATCCTCCAACACAGCCTACATGCAACTGAGCAGCCTGAC<br>ATCTGAGGACTCTGCAGTCTATTACTGTGCAACAGAGGGAGGTAATTGGGAG<br>GACTACTGGGGCCAAGGCACCACTCTCACAGTCTCCTCA |
| 69 | ADWA13 | CAGGTCCAGCTTCAGCAGTCTGGGGCTGAACTGGCAAAACCTGGGGCCTCAG<br>TGAAGATGTCCTGCAAGGCTTCTGGCTACACCTTTTCTAGCTACTGGATATA<br>TTGGGTAAAACAGAGGCCTGGACAGGTTCTGGAATGGATTGGATACATTAAT<br>CCTACCACTGGTTACACTGACTACAATCAGAAGTTCAAGGACAAGGCCACAT<br>TGACTGCAGACAAATCCTCCAGCACAGCCTACATGCAACTGAGCAGCCTGAC<br>ATCTGAGGACTCTGCAGTCTATTACTGTGCAACAGAGGGAGGTAATTGGGAG<br>GACTACTGGGGCCAAGGCACCACTCTCACAGTCTCCTCA |
| 70 | ADWA13-1 | CAGGTCCAGCTTCAGCAGTCTGGGGCTGAACTGGCAAAACCTGGGGCCTCAG<br>TGAAGATGTCCTGCAAGGCTTCTGGCTACACCTTTTCTAGCTACTGGATATA<br>TTGGGTAAAACAGAGGCCTGGACAGGTTCTGGAATGGATTGGATACATTAAT<br>CCTACCACTGGTTACACTGACTACAATCAGAAGTTCAAGGACAAGGCCACAT<br>TGACTGCAGACAAATCCTCCAGCACAGCCTACATGCAACTGAGCAGCCTGAC<br>ATCTGAGGACTCTACAGTCTATTACTGTGCAACAGAGGGAGGTAATTGGGAG<br>GACTACTGGGGCCAAGGCACCACTCTCACAGTCTCCTCA |
| 71 | ADWA13-2 | CAGGTCCAGCTTCAGCAGTCTGGGGCTGAACTGACAAAACCTGGGGCCTCAG<br>TGAAGATGTCCTGCAAGGCTTCTGGCTACACCTTTTCTAGCTACTGGATATA<br>TTGGGTAAAACAGAGGCCTGGACAGGTTCTGGAATGGATTGGATACATTAAT<br>CCTACCACTGGTTACACTGACTACAATCAGAAGTTCAAGGACAAGGCCACAT<br>TGACTGCAGACAAATCCTCCAGCACAGCCTACATGCAACTGAGCAGCCTGAC<br>ATCTGAGGACTCTGCAGTCTATTACTGTGCAACAGAGGGAGGTAATTGGGAG<br>GACTACTGGGGCCAAGGCACCACTCTCACAGTCTCCTCA |
| 72 | ADWA15 | CAGGTCCAACTGCAGCAGCCTGGGTCTGTGCTGGTGAGGCCTGGAGCTTCAG<br>TGAAGTTGTCCTGCAAGGCTTCTGGCTACACCTTCACCAGCTCCTGGATGCA<br>CTGGGCGAAGCAGAGGCCTGGACAAGGCCTTGAGTGGATTGGAGAGATTCAT<br>CCTAATAGTGGTAATAGTATCTACAATGAGAAGTTCAAGGACAAGGCCACAC<br>TGACTGTAGACACATCCTCCAGCACAGCCTACGTGGATCTCAGCAGCCTGAC<br>ATCTGAGGACTCTGCGGTCTATTACTGTGCAAGATGGGGGGATTTTGACTAC<br>TGGGGCCAAGGCACCACTCTCACAGTCTCCTCA |
| 73 | ADWA11 | GAGGTTCAGCTGCAGCAGTCTGGGGCTGAGCTTGTGAGGCCTGGGGCCTTTG<br>TCAAGTTGTCCTGCAAGGCTTCTGGCTTCAACATTAAAGACTACTATATGAA<br>TTGGGTGTTGCAGAGGCCTGAACAGGGCCTGGAGTGGATTGGATGGATTGAT<br>CCTGACAATGGTAATACTATATATGACCCGAAGTTCCAGGGCAAGGCCAGTA<br>TAACAGCAGACACATCCTCCAACACAGCCTACCTGCAGCTCAGCAGCCTGAC<br>ATCTGAGGACACTGCCGTCTATTACTGTGCTAGAAGACTACTTATGGACTAC<br>TGGGGTCAAGGAACCTCAGTCACCGTCTCCTCA |
| 74 | ADWA10 | GAGGTCCTGCTGCAACAGTCTGGACCTGAGCTGGTGAAGCCTGGGGCTTCAG<br>TGAAGATACCCTGCAAGGCTTCTGGATACACATTCACTAACTACAACATGGA<br>CTGGGTGAAGCAGAGCCATGGAAAGAGCCTTGAGTGGATTGGAGATATTAAT<br>CCTAACAGTGGTGGTTCTGTCTACAACCAGAAGTTCAAGGGCAAGGCCACAT<br>TGACTGTAGACAAGTCCTCCAGCACAGCCTACATGGAGCTCCGCAGCCTGAC<br>ATCTGAGGACACTGCAGTCTATTACTGTCAAGATGGGCCTACTATGGTGAA<br>AGGTTTCACTACTTTGACTACTGGGGCCAAGGCACCACTCTCACAGTCTCCT<br>CA |
| 75 | ADWA8 | CAGGTCCAACTGCAGCAACCTGGGTCTGAGCTGGTGAGGCCTGGAGCTTCAG<br>TGAAGCTGTCCTGCAAGGCTTCAGGCTACACATTCACCAGCTACTGGATGCA<br>CTGGGTGAAGCAGAGGCCTGGACAAGGCCTTGAGTGGATTGGAAATATTTAT<br>CCTGGTAGTGGTAGAACTAACTACGACGAGAAGTTCAAGAGCAAGGCCACAC<br>TGACTGTAGACACATCCTCCAGCACAGCCTACATGCAACTCAGCAGCCTGAC<br>ATCTGAGGACTCTGCGGTCTATTACTGTACAAGACCGCTCCAGTATAGGTAC<br>GACGTCTATCCTATGGACTACTGGGGTCAAGGAACCTCAGTCACCGTCTCCT<br>CA |
| 76 | ADWA8-1 | CAGGTCCAACTGCAGCAACCTGGGTCTGAGCTGGTGAGGCCTGGAGCTTCAG<br>TGAAGCTGTCCTGCAAGGCTTCAGGCTACACATTCACCAGCTACTGGATGCA<br>CTGGGTGAAGCAGAGGCCTGGACAAGGCCTTGAGTGGATTGGAAATATTTAT<br>CCTGGTAGTGGTAGAACTAACTACGACGAGAAGTTCAGGAGCAAGGCCACAC<br>TGACTGTAGACACATCCTCCAGCACAGCCTACATGCAACTCAGCAGCCTGAC<br>ATCTGAGGACTCTGCGGTCTATTACTGTACAAGACCGCTCCAGTATAGGTAC<br>GACGTCTATCCTATGGACTACTGGGGTCAAGGAACCTCAGTCACCGTCTCCT<br>CA |
| 77 | ADWA8-2 | CAGGTCCAACTGCAGCAACCTGGGTCTGAGCTGGTGAGGCCTGGAGCTTCAA<br>TGAAGCTGTCCTGCAAGGCTTCAGGCTACACATTCACCAGCTACTGGATGCA<br>CTGGGTGAAGCAGAGGCCTGGACAAGGCCTTGAGTGGATTGGAAATATTTAT<br>CCTGGTAGTGGTAGAACTAACTACGACGAGAAGTTCAAGAGCAAGGCCACAC<br>TGACTGTAGACACATCCTCCAGCACAGCCTACATGCAACTCACCAGCCTGAC<br>ATCTGAGGACTCTGCGGTCTATTACTGTACAAGACCGCTCCAGTATAGGTAC<br>GACGTCTATCCTATGGACTACTGGGGTCAAGGAACCTCAGTCACCGTCTCCT<br>CA |
| 78 | ADWA8-3 | CAGGTCCAACTGCAGCAACCTGGGTCTGAGCTGGTGAGGCCTGGAGCTTCAG<br>TGAAGCTGTCCTGCAAGGCTTCAGGCTACACATTCACCAGCTACTGGATGCA<br>CTGGGTGAAGCAGAAGCCTGGACAAGGCCTTGAGTGGATTGGAAATATTTAT<br>CCTGGTAGTGGTAGAACTAACTACGACGAGAAGTTCAAGAGCAAGGCCACAC<br>TGACTGTAGACACATCCTCCAGCACAGCCTACATGCAACTCACCAGCCTGAC |

TABLE 1 -continued

| SEQ ID NO: | Description | Sequence |
|---|---|---|
| | | ATCTGAGGACTCTGCGGTCTATTACTGTACAAGACCGCTCCAGTATAGGTAC GACGTCTATCCTATGGACTACTGGGGTCAAGGAACCTCAGTCACCGTCTCCT CA |
| 79 | ADWA20 | GATGTGCAGCTTCAGGAGTCGGGACCTGGCCTGGTGAAACCTTCTCAGTCTC TGTCCCTCACCTGCACTGTCACTGGCTACTCAATCACCAGTGATTTTGCCTG GAGCTGGATCCGGCAGTTTCCAGGAAACAAACTGGAGTGGATGGGCTACATA AGCTACAGTGGTAGCACTGGCTACAACCCATCTCTCAAAAGTCGAATCTCTA TCACTCGAGACACATCCAAGAACCAGTTCTTCCTGCAGTTGAATTCTGTGAC TACTGAGGACACAGCCACATATTACTGTACAAGAAGGGGCCTCTACCACTGG GGGTTTCCTTACTGGGGCCAAGGGACTCTGGTCACTGTCTCTGCA |
| 80 | ADWA25 | GAGGTGCAGCTGGTGGAGTCTGGGGGAGACTTAGTGAAGCCTGGAGGGTCCC TGAAACTCTCCTGTGCAGCCTCTGGATTCACTTTCAGTAGCTATGGCATGTC TTGGGTTCGCCAGACTCCAGACAAGAGGCTGGAGTGGGTCGCAACCATTAGT GGTGGTGGTAGTTACACCTACTATCCAGACAGTGTGAAGGGGCGATTCACCA TCTCCAGACACAATGCCAAGAACACCCTGTACCTGCAAATGAGCAGTCTGAA GTCTGAGGACACAGCCATGTATTACTGTCAAGCGACCCCTATTACTACGGT AGAAGGGACCTGGCCTGGATTGCTTACTGGGGCCAAGGGACTCTGGTCACTG TCTCTGCA |

V<sub>L</sub> SEQUENCES-NUCLEIC ACIDS

| 81 | ADWA2 ADWA13 ADWA16 | GATATCCAGATGACACAGACTACATCCTCCCTGTCTGCCTCTCTGGGAGACA GAGTCACCATCAGTTGCAGGGCAAGTCAGGATATTAGCAATTATTTAAACTG GTATCAGCAGAAACCAGATGGAACTGTTAAACTCCTGATCTATTACACATCT AGATTATACTCAGGAGTCCCATCAAGGTTCAGTGGCAGTGGGTCTGGGACAG ATTATTCTCTCACCATCAGCAACCTGGAACCTAAAGATATTGCCACTTACTA TTGTCAGCAGTTTAGTGAGCTTCCTCGGACGTTCGGTGGAGGCACCAAGCTG GAAATCAAA |
| 82 | ADWA15 | GATGTCCAGATGACACAGACTACATCCTCCCTGTCTGCCTCTCTGGGAGACA GAGTCACCATCAGTTGTAGGGCAAGTCAGGATATTAGCAATTATTTAAACTG GTATCAGCAGAAACCAGATGGAACTGTTAAACTCCTGATCTACTACACATCA CGATTACACTCAGGAGTCCCATCAAGGTTCAGTGGCAGTGGGTCTGGGACAG ATTTTTCTCTCACCATCAGCAACCTGGAACCTGAAGATATTGCCACTTACTA TTGTCAGCAATACAATAAGGTTCCGCTCACGTTCGGTGGTGGGACCAAGCTG GAGCTGAAA |
| 83 | ADWA11 | GATATTGTGATGACTCAGGCTGCACCCTCTGTACCTGTCACTCCTGGAGAGT CAGTTTCCATCTCCTGCAGGTCTACTAAGAGTCTTCTGCATTTTAATGGCAA CACTTACTTGTTTTGGTTCCTGCAGAGGCCAGGCCAGTCTCCTCAGCGCCTG ATATATTATATGTCCAACCTTGCCTCAGGAGTCCCAGACAGGTTCAGTGGCA GAGGGTCAGGAACTGATTTCACACTGAGAATCAGTAGAGTGGAGGCTGAGGA TGTGGGTGTTTATTACTGTATGCAAAGTCTAGAATATCCATTCACGTTCGGC ACGGGGACAAAATTGGAAATAAAA |
| 84 | ADWA10 | AGGTCACAATGACTTGCAGGGCCAGTTCAAGTGTAAGTTACATGCACTGGTA CCAGCAGAAGTCAGGATCCTCCCCCAAACCCTGGATTTATGCCACATCCAAC CTGGCTTCTGGAGTCCCTGCTCGCTTCAGTGGCAGTGGGTCTGGGACCTCTT ACTCTCTCACAATCAGCAGAGTGGAGGCTGAAGATGCTGCCACTTATTACTG CCAGCAGTGGAGTAGTAACCCACCCACGTTCGGAGGGGGGACCAAGCTGGAA ATAAAA |
| 85 | ADWA8 | GACATCCAGATGACTCAGTCTCCAGCTTCCCTGTCTGCATCTGTGGGAGAAA CTGTCACCATCACATGTCGAGCAAGTGAGAATATTGACAGTTATTTAGCATG GTATCAGCAGAAACAGGGAAAATCTCCTCAGCTCCTGGTCTATGCTGCAACA CTCTTACCAGATGGTGTGCCATCAAGGTTCAGTGGCAGTGGATCAGGCACAC AGTATTCTCTCAAGATCAACAGCCTGCAGTCTGAAGATGTTGCGAGATATTA CTGTCAACATTATTATAATACTCCGTGGACGTTCGGTGGAGGCACCAAGCTG GAAATCAAA |
| 86 | ADWA20 | GACATTGTGATGACCCAGTCTCACAAATTCATGTCCACATCAGTGGGAGACA GGGTCAGCATCACCTGCAAGGCCAGTCAGGATGTGAGTAGTGCTGTAGCCTG GTATCAACAAAAACCAGGGCAATCTCCTAAACTCCTGATTTACTGGGCATCC ACCCGGCACACTGGAGTCCCTGATCGCTTCACAGGCAGTGGATCTGGGACAG ATTATACTCTCACCGTCAGCAATGTGCAGGCTGAAGACCTGGCACTTTATTA CTGTCAGCAACATTATATCACTCCTTACACGTTCGGAGGGGGGACCAAGCTG GAAATAAAA |
| 87 | ADWA25 | GACATTGTGATGACCCAGTCTCAAAAATTCATGTCCACATCAGTAGGAGACA GGGTCAGCGTCACCTGCAAGGCCAGTCAGAATGTGGGTACTAATGTAGCCTG GTATCAACAGAAACCAGGGCAATCTCCTAAAGCACTGATTTACTCGGCATCC TACCGGTACAGTGGAGTCCCTGATCGCTTCACAGGCAGTGGATCTGGGACAG ATTTCACTCTCACCATCAGCAATGTGCAGTCTGAAGACTTGGCAGAGTATTT CTGTCAGCAATATAACAGCTATCCGTACACGTTCGGAGGGGGGACCAAGCTG GAAATAAAA |

The above examples are provided to illustrate the invention but not to limit its scope. Other variants of the invention will be readily apparent to one of ordinary skill in the art and are encompassed by the appended claims.

All publications, databases, internet sources, patents, patent applications, and accession numbers cited herein are hereby incorporated by reference in their entireties for all purposes.

What is claimed is:

1. An isolated antibody that specifically binds to human integrin β8 and inhibits adhesion of latency associated peptide (LAP) to αvβ8, wherein the antibody comprises:
   a heavy chain variable region comprising the Kabat-determined or Chothia-determined complementarity determining regions (HCDR1, HCDR2, and HCDR3) of SEQ ID NO:1 and a light chain variable region comprising the Kabat-determined or Chothia-determined complementarity determining regions (LCDR1, LCDR2, and LCDR3) of SEQ ID NO:16; or
   a heavy chain variable region comprising the Kabat-determined or Chothia-determined complementarity determining regions (HCDR1, HCDR2, and HCDR3) of SEQ ID NO:2 and a light chain variable region comprising the Kabat-determined or Chothia-determined complementarity determining regions (LCDR1, LCDR2, and LCDR3) of SEQ ID NO:16; or
   a heavy chain variable region comprising the Kabat-determined or Chothia-determined complementarity determining regions (HCDR1, HCDR2, and HCDR3) of SEQ ID NO:3 and a light chain variable region comprising the Kabat-determined or Chothia-determined complementarity determining regions (LCDR1, LCDR2, and LCDR3) of SEQ ID NO:16; or
   a heavy chain variable region comprising the Kabat-determined or Chothia-determined complementarity determining regions (HCDR1, HCDR2, and HCDR3) of SEQ ID NO:4 and a light chain variable region comprising the Kabat-determined or Chothia-determined complementarity determining regions (LCDR1, LCDR2, and LCDR3) of SEQ ID NO:16; or
   a heavy chain variable region comprising the Kabat-determined or Chothia-determined complementarity determining regions (HCDR1, HCDR2, and HCDR3) of SEQ ID NO:5 and a light chain variable region comprising the Kabat-determined or Chothia-determined complementarity determining regions (LCDR1, LCDR2, and LCDR3) of SEQ ID NO:16; or
   a heavy chain variable region comprising the Kabat-determined or Chothia-determined complementarity determining regions (HCDR1, HCDR2, and HCDR3) of SEQ ID NO:6 and a light chain variable region comprising the Kabat-determined or Chothia-determined complementarity determining regions (LCDR1, LCDR2, and LCDR3) of SEQ ID NO:16; or a heavy chain variable region comprising the Kabat-determined or Chothia-determined complementarity determining regions (HCDR1, HCDR2, and HCDR3) of SEQ ID NO:7 and a light chain variable region comprising the Kabat-determined or Chothia-determined complementarity determining regions (LCDR1, LCDR2, and LCDR3) of SEQ ID NO:17; or a heavy chain variable region comprising the Kabat-determined or Chothia-determined complementarity determining regions (HCDR1, HCDR2, and HCDR3) of SEQ ID NO:8 and a light chain variable region comprising the Kabat-determined or Chothia-determined complementarity determining regions (LCDR1, LCDR2, and LCDR3) of SEQ ID NO:18; or a heavy chain variable region comprising the Kabat-determined or Chothia-determined complementarity determining regions (HCDR1, HCDR2, and HCDR3) of SEQ ID NO:9 and a light chain variable region comprising the Kabat-determined or Chothia-determined complementarity determining regions (LCDR1, LCDR2, and LCDR3) of SEQ ID NO:19; or a heavy chain variable region comprising the Kabat-determined or Chothia-determined complementarity determining regions (HCDR1, HCDR2, and HCDR3) of SEQ ID NO:10 and a light chain variable region comprising the Kabat-determined or Chothia-determined complementarity determining regions (LCDR1, LCDR2, and LCDR3) of SEQ ID NO:20; or a heavy chain variable region comprising the Kabat-determined or Chothia-determined complementarity determining regions (HCDR1, HCDR2, and HCDR3) of SEQ ID NO:11 and a light chain variable region comprising the Kabat-determined or Chothia-determined complementarity determining regions (LCDR1, LCDR2, and LCDR3) of SEQ ID NO:20; or a heavy chain variable region comprising the Kabat-determined or Chothia-determined complementarity determining regions (HCDR1, HCDR2, and HCDR3) of SEQ ID NO:12 and a light chain variable region comprising the Kabat-determined or Chothia-determined complementarity determining regions (LCDR1, LCDR2, and LCDR3) of SEQ ID NO:20; or a heavy chain variable region comprising the Kabat-determined or Chothia-determined complementarity determining regions (HCDR1, HCDR2, and HCDR3) of SEQ ID NO:13 and a light chain variable region comprising the Kabat-determined or Chothia-determined complementarity determining regions (LCDR1, LCDR2, and LCDR3) of SEQ ID NO:20; or a heavy chain variable region comprising the Kabat-determined or Chothia-determined complementarity determining regions (HCDR1, HCDR2, and HCDR3) of SEQ ID NO:14 and a light chain variable region comprising the Kabat-determined or Chothia-determined complementarity determining regions (LCDR1, LCDR2, and LCDR3) of SEQ ID NO:21, or a heavy chain variable region comprising the Kabat-determined or Chothia-determined complementarity determining regions (HCDR1, HCDR2, and HCDR3) of SEQ ID NO:15 and a light chain variable region comprising the complementarity determining regions (LCDR1, LCDR2, and LCDR3) of SEQ ID NO:22.

2. The antibody of claim 1, wherein the antibody comprises one or more human framework regions.

3. A pharmaceutical composition comprising the antibody of claim 1.

4. The isolated antibody of claim 1, wherein
HCDR1 comprises SEQ ID NO:88, HCDR2 comprises SEQ ID NO:90, and HCDR3 comprises SEQ ID NO:25, and
LCDR1 comprises SEQ ID NO:46, LCDR2 comprises SEQ ID NO:47, and LCDR3 comprises SEQ ID NO:48.

5. The isolated antibody of claim 1, wherein
HCDR1 comprises SEQ ID NO:89, HCDR2 comprises SEQ ID NO:24, and HCDR3 comprises SEQ ID NO:25, and
LCDR1 comprises SEQ ID NO:46, LCDR2 comprises SEQ ID NO:47, and LCDR3 comprises SEQ ID NO:48.

6. The isolated antibody of claim 1, wherein
HCDR1 comprises SEQ ID NO:88, HCDR2 comprises SEQ ID NO:90, and HCDR3 comprises SEQ ID NO:25, and
LCDR1 comprises SEQ ID NO:46, LCDR2 comprises SEQ ID NO:47, and LCDR3 comprises SEQ ID NO:48.

7. The isolated antibody of claim 1, wherein
HCDR1 comprises SEQ ID NO:89, HCDR2 comprises SEQ ID NO:26, and HCDR3 comprises SEQ ID NO:25, and
LCDR1 comprises SEQ ID NO:46, LCDR2 comprises SEQ ID NO:47, and LCDR3 comprises SEQ ID NO:48.

8. The isolated antibody of claim 1, wherein
HCDR1 comprises SEQ ID NO:91, HCDR2 comprises SEQ ID NO:93, and HCDR3 comprises SEQ ID NO:29, and
LCDR1 comprises SEQ ID NO:46, LCDR2 comprises SEQ ID NO:49, and LCDR3 comprises SEQ ID NO:50.

9. The isolated antibody of claim 1, wherein
HCDR1 comprises SEQ ID NO:92, HCDR2 comprises SEQ ID NO:28, and HCDR3 comprises SEQ ID NO:29, and
LCDR1 comprises SEQ ID NO:46, LCDR2 comprises SEQ ID NO:49, and LCDR3 comprises SEQ ID NO:50.

10. The isolated antibody of claim 1, wherein
HCDR1 comprises SEQ ID NO:94, HCDR2 comprises SEQ ID NO:96, and HCDR3 comprises SEQ ID NO:32, and
LCDR1 comprises SEQ ID NO:51, LCDR2 comprises SEQ ID NO:52, and LCDR3 comprises SEQ ID NO:53.

11. The isolated antibody of claim 1, wherein
HCDR1 comprises SEQ ID NO:95, HCDR2 comprises SEQ ID NO:31, and HCDR3 comprises SEQ ID NO:32, and
LCDR1 comprises SEQ ID NO:51, LCDR2 comprises SEQ ID NO:52, and LCDR3 comprises SEQ ID NO:53.

12. The isolated antibody of claim 1, wherein
HCDR1 comprises SEQ ID NO:97, HCDR2 comprises SEQ ID NO:99, and HCDR3 comprises SEQ ID NO:35, and
LCDR1 comprises SEQ ID NO:54, LCDR2 comprises SEQ ID NO:55, and LCDR3 comprises SEQ ID NO:56.

13. The isolated antibody of claim 1, wherein
HCDR1 comprises SEQ ID NO:98, HCDR2 comprises SEQ ID NO:34, and HCDR3 comprises SEQ ID NO:35, and
LCDR1 comprises SEQ ID NO:54, LCDR2 comprises SEQ ID NO:55, and LCDR3 comprises SEQ ID NO:56.

14. The isolated antibody of claim 1, wherein
HCDR1 comprises SEQ ID NO:100, HCDR2 comprises SEQ ID NO:102, and HCDR3 comprises SEQ ID NO:38, and
LCDR1 comprises SEQ ID NO:57, LCDR2 comprises SEQ ID NO:58, and LCDR3 comprises SEQ ID NO:59.

15. The isolated antibody of claim 1, wherein
HCDR1 comprises SEQ ID NO:101, HCDR2 comprises SEQ ID NO:37, and HCDR3 comprises SEQ ID NO:38, and
LCDR1 comprises SEQ ID NO:57, LCDR2 comprises SEQ ID NO:58, and LCDR3 comprises SEQ ID NO:59.

16. The isolated antibody of claim 1, wherein
HCDR1 comprises SEQ ID NO:101, HCDR2 comprises SEQ ID NO:39, and HCDR3 comprises SEQ ID NO:38, and
LCDR1 comprises SEQ ID NO:57, LCDR2 comprises SEQ ID NO:58, and LCDR3 comprises SEQ ID NO:59.

17. The isolated antibody of claim 1, wherein
HCDR1 comprises SEQ ID NO:103, HCDR2 comprises SEQ ID NO:105, and HCDR3 comprises SEQ ID NO:42, and
LCDR1 comprises SEQ ID NO:60, LCDR2 comprises SEQ ID NO:61, and LCDR3 comprises SEQ ID NO:62.

18. The isolated antibody of claim 1, wherein
HCDR1 comprises SEQ ID NO:104, HCDR2 comprises SEQ ID NO:41, and HCDR3 comprises SEQ ID NO:42, and
LCDR1 comprises SEQ ID NO:60, LCDR2 comprises SEQ ID NO:61, and LCDR3 comprises SEQ ID NO:62.

19. The isolated antibody of claim 1, wherein
HCDR1 comprises SEQ ID NO:106, HCDR2 comprises SEQ ID NO:108, and HCDR3 comprises SEQ ID NO:45, and
LCDR1 comprises SEQ ID NO:63, LCDR2 comprises SEQ ID NO:64, and LCDR3 comprises SEQ ID NO:65.

20. The isolated antibody of claim 1, wherein
HCDR1 comprises SEQ ID NO:107, HCDR2 comprises SEQ ID NO:44, and HCDR3 comprises SEQ ID NO:45, and
LCDR1 comprises SEQ ID NO:63, LCDR2 comprises SEQ ID NO:64, and LCDR3 comprises SEQ ID NO:65.

* * * * *

SEQUENCE LISTING

<160> NUMBER OF SEQ ID NOS: 108

<210> SEQ ID NO 1
<211> LENGTH: 117
<212> TYPE: PRT
<213> ORGANISM: Mus Musculus

<400> SEQUENCE: 1

Gln Val Gln Leu Gln Gln Ser Gly Ala Glu Leu Ala Lys Pro Gly Ala
1               5                   10                  15

Ser Met Lys Met Ser Cys Lys Ala Ser Gly Tyr Thr Phe Ser Ser Tyr
            20                  25                  30

Trp Ile Tyr Trp Val Lys Gln Arg Pro Gly Gln Gly Leu Glu Trp Ile
        35                  40                  45

Gly Tyr Ile Asn Pro Thr Thr Gly Tyr Thr Glu Tyr Asn Gln Lys Phe
    50                  55                  60

Arg Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 2
<211> LENGTH: 117
<212> TYPE: PRT
<213> ORGANISM: Mus musculus

<400> SEQUENCE: 2

Gln Val Gln Leu Gln Gln Ser Gly Ala Glu Leu Ala Lys Pro Gly Ala
1               5                   10                  15

Ser Met Lys Met Ser Cys Lys Ala Ser Gly Tyr Thr Phe Ser Ser Tyr
            20                  25                  30

Trp Ile Tyr Trp Val Lys Gln Arg Pro Gly Gln Gly Leu Glu Trp Ile
        35                  40                  45

Gly Tyr Ile Asn Pro Thr Thr Gly Tyr Thr Glu Tyr Asn Gln Lys Phe
    50                  55                  60

Arg Asp Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 3
<211> LENGTH: 117
<212> TYPE: PRT
<213> ORGANISM: Mus musculus

<400> SEQUENCE: 3

Gln Val Gln Leu Gln Gln Ser Gly Ala Glu Leu Thr Lys Pro Gly Ala
1               5                   10                  15

Ser Met Lys Met Ser Cys Lys Ala Ser Gly Tyr Thr Phe Ser Ser Tyr
            20                  25                  30

Trp Ile Tyr Trp Val Lys Gln Arg Pro Gly Gln Gly Leu Glu Trp Ile
            35                  40                  45

Gly Tyr Ile Asn Pro Thr Thr Gly Tyr Thr Glu Tyr Asn Gln Lys Phe
        50                  55                  60

Arg Asp Lys Val Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 4
<211> LENGTH: 117
<212> TYPE: PRT
<213> ORGANISM: Mus musculus

<400> SEQUENCE: 4

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Ile Tyr Trp Val Lys Gln Arg Pro Gly Gln Val Leu Glu Trp Ile
            35                  40                  45

Gly Tyr Ile Asn Pro Thr Thr Gly Tyr Thr Asp Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 5
<211> LENGTH: 117
<212> TYPE: PRT
<213> ORGANISM: Mus musculus

<400> SEQUENCE: 5

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Ile Tyr Trp Val Lys Gln Arg Pro Gly Gln Val Leu Glu Trp Ile
            35                  40                  45

Gly Tyr Ile Asn Pro Thr Thr Gly Tyr Thr Asp Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Thr Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 6
<211> LENGTH: 117
<212> TYPE: PRT
<213> ORGANISM: Mus musculus

<400> SEQUENCE: 6

Gln Val Gln Leu Gln Gln Ser Gly Ala Glu Leu Thr Lys Pro Gly Ala
1               5                   10                  15

Ser Val Lys Met Ser Cys Lys Ala Ser Gly Tyr Thr Phe Ser Ser Tyr
            20                  25                  30

Trp Ile Tyr Trp Val Lys Gln Arg Pro Gly Gln Val Leu Glu Trp Ile
        35                  40                  45

Gly Tyr Ile Asn Pro Thr Thr Gly Tyr Thr Asp Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Thr Val Tyr Tyr Cys
                85                  90                  95

Ala Thr Glu Gly Gly Asn Trp Glu Asp Tyr Trp Gly Gln Gly Thr Thr
            100                 105                 110

Leu Thr Val Ser Ser
        115

<210> SEQ ID NO 7
<211> LENGTH: 115
<212> TYPE: PRT
<213> ORGANISM: Mus musculus

<400> SEQUENCE: 7

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly Glu Ile His Pro Asn Ser Gly Asn Ser Ile Tyr Asn Glu Lys Phe
    50                  55                  60

Lys Asp Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Trp Gly Asp Phe Asp Tyr Trp Gly Gln Gly Thr Thr Leu Thr
            100                 105                 110

Val Ser Ser
        115

<210> SEQ ID NO 8
<211> LENGTH: 115
<212> TYPE: PRT
<213> ORGANISM: Mus musculus

<400> SEQUENCE: 8

Glu Val Gln Leu Gln Gln Ser Gly Ala Glu Leu Val Arg Pro Gly Ala
1               5                   10                  15

```
Phe Val Lys Leu Ser Cys Lys Ala Ser Gly Phe Asn Ile Lys Asp Tyr
            20                  25                  30

Tyr Met Asn Trp Val Leu Gln Arg Pro Glu Gln Gly Leu Glu Trp Ile
        35                  40                  45

Gly Trp Ile Asp Pro Asp Asn Gly Asn Thr Ile Tyr Asp Pro Lys Phe
50                      55                  60

Gln Gly Lys Ala Ser Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Leu Leu Met Asp Tyr Trp Gly Gln Gly Thr Ser Val Thr
            100                 105                 110

Val Ser Ser
        115
```

<210> SEQ ID NO 9
<211> LENGTH: 122
<212> TYPE: PRT
<213> ORGANISM: Mus musculus

<400> SEQUENCE: 9

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asn Tyr
            20                  25                  30

Asn Met Asp Trp Val Lys Gln Ser His Gly Lys Ser Leu Glu Trp Ile
        35                  40                  45

Gly Asp Ile Asn Pro Asn Ser Gly Gly Ser Val Tyr Asn Gln Lys Phe
50                      55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Trp Ala Tyr Tyr Gly Glu Arg Phe His Tyr Phe Asp Tyr Trp
            100                 105                 110

Gly Gln Gly Thr Thr Leu Thr Val Ser Ser
        115                 120
```

<210> SEQ ID NO 10
<211> LENGTH: 122
<212> TYPE: PRT
<213> ORGANISM: Mus musculus

<400> SEQUENCE: 10

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Arg Thr Asn Tyr Asp Glu Lys Phe
50                      55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

Thr Arg Pro Leu Gln Tyr Arg Tyr Asp Val Tyr Pro Met Asp Tyr Trp
            100                 105                 110

Gly Gln Gly Thr Ser Val Thr Val Ser Ser
        115                 120

<210> SEQ ID NO 11
<211> LENGTH: 122
<212> TYPE: PRT
<213> ORGANISM: Mus musculus

<400> SEQUENCE: 11

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Arg Thr Asn Tyr Asp Glu Lys Phe
    50                  55                  60

Arg Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Pro Leu Gln Tyr Arg Tyr Asp Val Tyr Pro Met Asp Tyr Trp
            100                 105                 110

Gly Gln Gly Thr Ser Val Thr Val Ser Ser
        115                 120

<210> SEQ ID NO 12
<211> LENGTH: 122
<212> TYPE: PRT
<213> ORGANISM: Mus musculus

<400> SEQUENCE: 12

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Lys Pro Gly Gln Gly Leu Glu Trp Ile
        35                  40                  45

Gly Asn Ile Tyr Pro Gly Ser Gly Arg Thr Asn Tyr Asp Glu Lys Phe
    50                  55                  60

Lys Ser Lys Ala Thr Leu Thr Val Asp Thr Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Thr Arg Pro Leu Gln Tyr Arg Tyr Asp Val Tyr Pro Met Asp Tyr Trp
            100                 105                 110

Gly Gln Gly Thr Ser Val Thr Val Ser Ser
        115                 120

<210> SEQ ID NO 13
<211> LENGTH: 122
<212> TYPE: PRT
<213> ORGANISM: Mus musculus

<400> SEQUENCE: 13

Gln Val Gln Leu Gln Gln Pro Gly Ser Glu Leu Val Arg Pro Gly Ala

```
                1               5                      10                     15
            Ser Met Lys Leu Ser Cys Lys Ala Ser Gly Tyr Thr Phe Thr Ser Tyr
                        20                  25                  30

Trp Met His Trp Val Lys Gln Arg Pro Gly Gln Gly Leu Glu Trp Ile
                        35                  40                  45

Gly Asn Ile Tyr Pro Gly Ser Gly Arg Thr Asn Tyr Asp Glu Lys Phe
                        50                  55                  60

Lys Ser Lys Ala Thr Leu Thr Val Asp Thr Ser Ser Ser Thr Ala Tyr
            65                      70                  75                  80

Met Gln Leu Thr Ser Leu Thr Ser Glu Asp Ser Ala Val Tyr Tyr Cys
                        85                  90                  95

Thr Arg Pro Leu Gln Tyr Arg Tyr Asp Val Tyr Pro Met Asp Tyr Trp
                        100                 105                 110

Gly Gln Gly Thr Ser Val Thr Val Ser Ser
                        115                 120

<210> SEQ ID NO 14
<211> LENGTH: 119
<212> TYPE: PRT
<213> ORGANISM: Mus musculus

<400> SEQUENCE: 14

Asp Val Gln Leu Gln Glu Ser Gly Pro Gly Leu Val Lys Pro Ser Gln
            1               5                   10                  15

Ser Leu Ser Leu Thr Cys Thr Val Thr Gly Tyr Ser Ile Thr Ser Asp
                        20                  25                  30

Phe Ala Trp Ser Trp Ile Arg Gln Phe Pro Gly Asn Lys Leu Glu Trp
                        35                  40                  45

Met Gly Tyr Ile Ser Tyr Ser Gly Ser Thr Gly Tyr Asn Pro Ser Leu
                        50                  55                  60

Lys Ser Arg Ile Ser Ile Thr Arg Asp Thr Ser Lys Asn Gln Phe Phe
            65                      70                  75                  80

Leu Gln Leu Asn Ser Val Thr Thr Glu Asp Thr Ala Thr Tyr Tyr Cys
                        85                  90                  95

Thr Arg Arg Gly Leu Tyr His Trp Gly Phe Pro Tyr Trp Gly Gln Gly
                        100                 105                 110

Thr Leu Val Thr Val Ser Ala
                        115

<210> SEQ ID NO 15
<211> LENGTH: 124
<212> TYPE: PRT
<213> ORGANISM: Mus musculus

<400> SEQUENCE: 15

Glu Val Gln Leu Val Glu Ser Gly Gly Asp Leu Val Lys Pro Gly Gly
            1               5                   10                  15

Ser Leu Lys Leu Ser Cys Ala Ala Ser Gly Phe Thr Phe Ser Ser Tyr
                        20                  25                  30

Gly Met Ser Trp Val Arg Gln Thr Pro Asp Lys Arg Leu Glu Trp Val
                        35                  40                  45

Ala Thr Ile Ser Gly Gly Gly Ser Tyr Thr Tyr Tyr Pro Asp Ser Val
                        50                  55                  60

Lys Gly Arg Phe Thr Ile Ser Arg His Asn Ala Lys Asn Thr Leu Tyr
            65                      70                  75                  80

Leu Gln Met Ser Ser Leu Lys Ser Glu Asp Thr Ala Met Tyr Tyr Cys
```

```
                85                  90                  95

Ala Ser Asp Pro Tyr Tyr Gly Arg Arg Asp Leu Ala Trp Ile Ala
            100                 105                 110

Tyr Trp Gly Gln Gly Thr Leu Val Thr Val Ser Ala
        115                 120

<210> SEQ ID NO 16
<211> LENGTH: 107
<212> TYPE: PRT
<213> ORGANISM: Mus musculus

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Lys Asp Ile Ala Thr Tyr Tyr Cys Gln Gln Phe Ser Glu Leu Pro Arg
                85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Mus musculus

<400> SEQUENCE: 17

Asp Val Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Pro
65                  70                  75                  80

Glu Asp Ile Ala Thr Tyr Tyr Cys Gln Gln Tyr Asn Lys Val Pro Leu
                85                  90                  95

Thr Phe Gly Gly Gly Thr Lys Leu Glu Leu Lys
            100                 105

<210> SEQ ID NO 18
<211> LENGTH: 112
<212> TYPE: PRT
<213> ORGANISM: Mus musculus

<400> SEQUENCE: 18

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Phe
            20                  25                  30
```

```
Asn Gly Asn Thr Tyr Leu Phe Trp Phe Leu Gln Arg Pro Gly Gln Ser
            35                  40                  45

Pro Gln Arg Leu Ile Tyr Tyr Met Ser Asn Leu Ala Ser Gly Val Pro
 50                  55                  60

Asp Arg Phe Ser Gly Arg Gly Ser Gly Thr Asp Phe Thr Leu Arg Ile
 65                  70                  75                  80

Ser Arg Val Glu Ala Glu Asp Val Gly Val Tyr Tyr Cys Met Gln Ser
                 85                  90                  95

Leu Glu Tyr Pro Phe Thr Phe Gly Thr Gly Thr Lys Leu Glu Ile Lys
            100                 105                 110

<210> SEQ ID NO 19
<211> LENGTH: 106
<212> TYPE: PRT
<213> ORGANISM: Mus musculus

<400> SEQUENCE: 19

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
                 20                  25                  30

His Trp Tyr Gln Gln Lys Ser Gly Ser Ser Pro Lys Pro Trp Ile Tyr
             35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Gly Gly Thr Lys Leu Glu Ile Lys
            100                 105

<210> SEQ ID NO 20
<211> LENGTH: 107
<212> TYPE: PRT
<213> ORGANISM: Mus musculus

<400> SEQUENCE: 20

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Asp Ser Tyr
                 20                  25                  30

Leu Ala Trp Tyr Gln Gln Lys Gln Gly Lys Ser Pro Gln Leu Leu Val
             35                  40                  45

Tyr Ala Ala Thr Leu Leu Pro Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Val Ala Arg Tyr Tyr Cys Gln His Tyr Tyr Asn Thr Pro Trp
                 85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Mus musculus
```

<400> SEQUENCE: 21

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Val Ser Asn Val Gln Ala
65                  70                  75                  80

Glu Asp Leu Ala Leu Tyr Tyr Cys Gln Gln His Tyr Ile Thr Pro Tyr
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: Mus musculus

<400> SEQUENCE: 22

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 23
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 23

Gly Tyr Thr Phe Ser Ser Tyr Trp Ile Tyr
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 24

Tyr Ile Asn Pro Thr Thr Gly Tyr Thr Glu Tyr Asn Gln Lys Phe Arg
1               5                   10                  15

Asp

<210> SEQ ID NO 25
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 25

Glu Gly Gly Asn Trp Glu Asp Tyr
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 26

Tyr Ile Asn Pro Thr Thr Gly Tyr Thr Asp Tyr Asn Gln Lys Phe Lys
1               5                   10                  15

Asp

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 27

Gly Tyr Thr Phe Thr Ser Ser Trp Met His
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 28

Glu Ile His Pro Asn Ser Gly Asn Ser Ile Tyr Asn Glu Lys Phe Lys
1               5                   10                  15

Asp

<210> SEQ ID NO 29
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 29

Trp Gly Asp Phe Asp Tyr
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic polypeptide

```
<400> SEQUENCE: 30

Gly Phe Asn Ile Lys Asp Tyr Tyr Met Asn
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 31

Trp Ile Asp Pro Asp Asn Gly Asn Thr Ile Tyr Asp Pro Lys Phe Gln
1               5                   10                  15

Gly

<210> SEQ ID NO 32
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 32

Arg Leu Leu Met Asp Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 33

Gly Tyr Thr Phe Thr Asn Tyr Asn Met Asp
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 34

Asp Ile Asn Pro Asn Ser Gly Gly Ser Val Tyr Asn Gln Lys Phe Lys
1               5                   10                  15

Gly

<210> SEQ ID NO 35
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 35

Trp Ala Tyr Tyr Gly Glu Arg Phe His Tyr Phe Asp Tyr
1               5                   10

<210> SEQ ID NO 36
<211> LENGTH: 10
<212> TYPE: PRT
<213> ORGANISM: Artificial Sequence
```

```
<220> FEATURE:
<223> OTHER INFORMATION: Synthetic polypeptide

<400> SEQUENCE: 36

Gly Tyr Thr Phe Thr Ser Tyr Trp Met His
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 37

Asn Ile Tyr Pro Gly Ser Gly Arg Thr Asn Tyr Asp Glu Lys Phe Lys
1               5                   10                  15
Ser

<210> SEQ ID NO 38
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 38

Pro Leu Gln Tyr Arg Tyr Asp Val Tyr Pro Met Asp Tyr
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 39

Asn Ile Tyr Pro Gly Ser Gly Arg Thr Asn Tyr Asp Glu Lys Phe Arg
1               5                   10                  15
Ser

<210> SEQ ID NO 40
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 40

Gly Tyr Ser Ile Thr Ser Asp Phe Ala Trp Ser
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 41

Tyr Ile Ser Tyr Ser Gly Ser Thr Gly Tyr Asn Pro Ser Leu Lys Ser
1               5                   10                  15

<210> SEQ ID NO 42
```

<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 42

Arg Gly Leu Tyr His Trp Gly Phe Pro Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 43

Gly Phe Thr Phe Ser Ser Tyr Gly Met Ser
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 44

Thr Ile Ser Gly Gly Gly Ser Tyr Thr Tyr Tyr Pro Asp Ser Val Lys
1               5                   10                  15

Gly

<210> SEQ ID NO 45
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 45

Asp Pro Tyr Tyr Tyr Gly Arg Arg Asp Leu Ala Trp Ile Ala Tyr
1               5                   10                  15

<210> SEQ ID NO 46
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 46

Arg Ala Ser Gln Asp Ile Ser Asn Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 47

Tyr Thr Ser Arg Leu Tyr Ser
1               5

```
<210> SEQ ID NO 48
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 48

Gln Gln Phe Ser Glu Leu Pro Arg Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 49

Tyr Thr Ser Arg Leu His Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 50

Gln Gln Tyr Asn Lys Val Pro Leu Thr
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 51

Arg Ser Thr Lys Ser Leu Leu His Phe Asn Gly Asn Thr Tyr Leu Phe
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Tyr Met Ser Asn Leu Ala Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 53

Met Gln Ser Leu Glu Tyr Pro Phe Thr
1               5

<210> SEQ ID NO 54
```

<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 54

Arg Ala Ser Ser Ser Val Ser Tyr Met His
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 55

Ala Thr Ser Asn Leu Ala Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 56

Gln Gln Trp Ser Ser Asn Pro Pro Thr
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 57

Arg Ala Ser Glu Asn Ile Asp Ser Tyr Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 58

Ala Ala Thr Leu Leu Pro Asp
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 59

Gln His Tyr Tyr Asn Thr Pro Trp Thr
1               5

<210> SEQ ID NO 60
<211> LENGTH: 11

```
<212> TYPE: PRT
<213> ORGANISM: Artificial Sequence
<220> FEATURE:
<223> OTHER INFORMATION: Synthetic polypeptide

<400> SEQUENCE: 60

Lys Ala Ser Gln Asp Val Ser Ser Ala Val Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 61

Trp Ala Ser Thr Arg His Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 62

Gln Gln His Tyr Ile Thr Pro Tyr Thr
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 63

Lys Ala Ser Gln Asn Val Gly Thr Asn Val Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 64

Ser Ala Ser Tyr Arg Tyr Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 65

Gln Gln Tyr Asn Ser Tyr Pro Tyr Thr
1               5

<210> SEQ ID NO 66
<211> LENGTH: 351
<212> TYPE: DNA
```

<213> ORGANISM: Artificial Sequence
<220> FEATURE:
<223> OTHER INFORMATION: Synthetic polynucleotide

<400> SEQUENCE: 66

```
caggtccagc ttcagcagtc tggggctgaa ctggcaaaac ctggggcctc aatgaagatg     60
tcctgcaagg cttctggcta caccttttct agctactgga tatattgggt aaaacagagg    120
cctggacagg gtctggaatg gattggatac attaatccta ccactggtta tactgagtac    180
aatcagaagt tcagggacaa ggccacattg actgcagaca atcctccaa cacagcctac     240
atgcaactga gcagcctgac atctgaggac tctgcagtct attactgtgc aacagaggga    300
ggtaattggg aggactactg gggccaaggc accactctca cagtctcctc a             351
```

<210> SEQ ID NO 67
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 67

```
caggtccagc ttcagcagtc tggggctgaa ctggcaaaac ctggggcctc aatgaagatg     60
tcctgcaagg cttctggcta caccttttct agctactgga tatattgggt aaaacagagg    120
cctggacagg gtctggaatg gattggatac attaatccta ccactggtta tactgagtac    180
aatcagaagt tcagggacaa ggtcacattg actgcagaca atcctccaa cacagcctac     240
atgcaactga gcagcctgac atctgaggac tctgcagtct attactgtgc aacagaggga    300
ggtaattggg aggactactg gggccaaggc accactctca cagtctcctc a             351
```

<210> SEQ ID NO 68
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 68

```
caggtccagc ttcagcagtc tggggctgaa ctgacaaaac ctggggcctc aatgaagatg     60
tcctgcaagg cttctggcta caccttttct agctactgga tatattgggt aaaacagagg    120
cctggacagg gtctggaatg gattggatac attaatccta ccactggtta tactgagtac    180
aatcagaagt tcagggacaa ggccacattg actgcagaca atcctccaa cacagcctac     240
atgcaactga gcagcctgac atctgaggac tctgcagtct attactgtgc aacagaggga    300
ggtaattggg aggactactg gggccaaggc accactctca cagtctcctc a             351
```

<210> SEQ ID NO 69
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 69

```
caggtccagc ttcagcagtc tggggctgaa ctggcaaaac ctggggcctc agtgaagatg     60
tcctgcaagg cttctggcta caccttttct agctactgga tatattgggt aaaacagagg    120
cctggacagg ttctggaatg gattggatac attaatccta ccactggtta cactgactac    180
aatcagaagt tcaaggacaa ggccacattg actgcagaca atcctccag cacagcctac     240
```

```
atgcaactga gcagcctgac atctgaggac tctgcagtct attactgtgc aacagaggga      300
ggtaattggg aggactactg gggccaaggc accactctca cagtctcctc a               351
```

<210> SEQ ID NO 70
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 70

```
caggtccagc ttcagcagtc tggggctgaa ctggcaaaac ctggggcctc agtgaagatg       60
tcctgcaagg cttctggcta cacctttcct agctactgga tatattgggt aaaacagagg      120
cctggacagt ttctggaatg gattggatac attaatccta ccactggtta cactgactac      180
aatcagaagt tcaaggacaa ggccacattg actgcagaca atcctccag cacagcctac       240 atgcaactga gcagcctgac atctgaggac tctacagtct attactgtgc aacagaggga      300
ggtaattggg aggactactg gggccaaggc accactctca cagtctcctc a               351
```

<210> SEQ ID NO 71
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 71

```
caggtccagc ttcagcagtc tggggctgaa ctgacaaaac ctggggcctc agtgaagatg       60
tcctgcaagg cttctggcta cacctttcct agctactgga tatattgggt aaaacagagg      120
cctggacagt ttctggaatg gattggatac attaatccta ccactggtta cactgactac      180
aatcagaagt tcaaggacaa ggccacattg actgcagaca atcctccag cacagcctac       240 atgcaactga gcagcctgac atctgaggac tctgcagtct attactgtgc aacagaggga      300
ggtaattggg aggactactg gggccaaggc accactctca cagtctcctc a               351
```

<210> SEQ ID NO 72
<211> LENGTH: 345
<212> TYPE: DNA
<213> ORGANISM: Artificial Sequence
<220> FEATURE:
<223> OTHER INFORMATION: Synthetic polynucleotide

<400> SEQUENCE: 72

```
caggtccaac tgcagcagcc tgggtctgtg ctggtgaggc ctggagcttc agtgaagttg       60
tcctgcaagg cttctggcta caccttcacc agctcctgga tgcactgggc gaagcagagg      120
cctggacaag gccttgagtg gattggagag attcatccta atagtggtaa tagtatctac      180
aatgagaagt tcaaggacaa ggccacactg actgtagaca catcctccag cacagcctac      240
gtggatctca gcagcctgac atctgaggac tctgcggtct attactgtgc aagatggggg      300
gattttgact actggggcca aggcaccact ctcacagtct cctca                      345
```

<210> SEQ ID NO 73
<211> LENGTH: 345
<212> TYPE: DNA
<213> ORGANISM: Artificial Sequence
<220> FEATURE:
<223> OTHER INFORMATION: Synthetic polynucleotide

<400> SEQUENCE: 73

```
gaggttcagc tgcagcagtc tggggctgag cttgtgaggc ctggggcctt tgtcaagttg    60
tcctgcaagg cttctggctt caacattaaa gactactata tgaattgggt gttgcagagg   120
cctgaacagg gcctggagtg gattggatgg attgatcctg acaatggtaa tactatatat   180
gacccgaagt tccagggcaa ggccagtata acagcagaca catcctccaa cacagcctac   240
ctgcagctca gcagcctgac atctgaggac actgccgtct attactgtgc tagaagacta   300
cttatggact actggggtca aggaacctca gtcaccgtct cctca                   345
```

<210> SEQ ID NO 74
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 74

```
gaggtcctgc tgcaacagtc tggacctgag ctggtgaagc ctggggcttc agtgaagata    60
ccctgcaagg cttctggata cacattcact aactacaaca tggactgggt gaagcagagc   120
catggaaaga gccttgagtg gattggagat attaatccta acagtggtgg ttctgtctac   180
aaccagaagt tcaagggcaa ggccacattg actgtagaca gtcctccag cacagcctac    240
atggagctcc gcagcctgac atctgaggac actgcagtct attactgtgc aagatggggcc  300
tactatggtg aaaggtttca ctactttgac tactggggcc aaggcaccac tctcacagtc   360
tcctca                                                              366
```

<210> SEQ ID NO 75
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 75

```
caggtccaac tgcagcaacc tgggtctgag ctggtgaggc ctggagcttc agtgaagctg    60
tcctgcaagg cttcaggcta cacattcacc agctactgga tgcactgggt gaagcagagg   120
cctggacaag gccttgagtg gattggaaat atttatcctg gtagtggtag aactaactac   180
gacgagaagt tcaagagcaa ggccacactg actgtagaca catcctccag cacagcctac   240
atgcaactca gcagcctgac atctgaggac tctgcggtct attactgtac aagaccgctc   300
cagtataggt acgacgtcta tcctatggac tactggggtc aaggaacctc agtcaccgtc   360
tcctca                                                              366
```

<210> SEQ ID NO 76
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 76

```
caggtccaac tgcagcaacc tgggtctgag ctggtgaggc ctggagcttc agtgaagctg    60
tcctgcaagg cttcaggcta cacattcacc agctactgga tgcactgggt gaagcagagg   120
cctggacaag gccttgagtg gattggaaat atttatcctg gtagtggtag aactaactac   180
gacgagaagt tcaggagcaa ggccacactg actgtagaca catcctccag cacagcctac   240
```

```
atgcaactca gcagcctgac atctgaggac tctgcggtct attactgtac aagaccgctc    300
cagtataggt acgacgtcta tcctatggac tactggggtc aaggaacctc agtcaccgtc    360
tcctca                                                               366
```

<210> SEQ ID NO 77
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 77

```
caggtccaac tgcagcaacc tgggtctgag ctggtgaggc ctggagcttc aatgaagctg     60
tcctgcaagg cttcaggcta cacattcacc agctactgga tgcactgggt gaagcagagg    120
cctggacaag gccttgagtg gattggaaat atttatcctg gtagtggtag aactaactac    180
gacgagaagt tcaagagcaa ggccacactg actgtagaca catcctccag cacagcctac    240
atgcaactca ccagcctgac atctgaggac tctgcggtct attactgtac aagaccgctc    300
cagtataggt acgacgtcta tcctatggac tactggggtc aaggaacctc agtcaccgtc    360
tcctca                                                               366
```

<210> SEQ ID NO 78
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 78

```
caggtccaac tgcagcaacc tgggtctgag ctggtgaggc ctggagcttc agtgaagctg     60
tcctgcaagg cttcaggcta cacattcacc agctactgga tgcactgggt gaagcagaag    120
cctggacaag gccttgagtg gattggaaat atttatcctg gtagtggtag aactaactac    180
gacgagaagt tcaagagcaa ggccacactg actgtagaca catcctccag cacagcctac    240
atgcaactca ccagcctgac atctgaggac tctgcggtct attactgtac aagaccgctc    300
cagtataggt acgacgtcta tcctatggac tactggggtc aaggaacctc agtcaccgtc    360
tcctca                                                               366
```

<210> SEQ ID NO 79
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 79

```
gatgtgcagc ttcaggagtc gggacctggc ctggtgaaac cttctcagtc tctgtccctc     60
acctgcactg tcactggcta ctcaatcacc agtgattttg cctggagctg gatccggcag    120
tttccaggaa acaaactgga gtggatgggc tacataagct acagtggtag cactggctac    180
aacccatctc tcaaaagtcg aatctctatc actcgagaca catccaagaa ccagttcttc    240
ctgcagttga attctgtgac tactgaggac acagccacat attactgtac aagaaggggc    300
ctctaccact gggggtttcc ttactggggc caagggactc tggtcactgt ctctgca       357
```

<210> SEQ ID NO 80

```
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 80
gaggtgcagc tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg gtcgcaacc attagtggtg gtggtagtta cacctactat     180
ccagacagtg tgaaggggcg attcaccatc tccagacaca tgccaagaa caccctgtac     240
ctgcaaatga gcagtctgaa gtctgaggac acagccatgt attactgtgc aagcgacccc    300
tattactacg gtagaaggga cctggcctgg attgcttact ggggccaagg gactctggtc     360
actgtctctg ca                                                         372

<210> SEQ ID NO 81
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 81
gatatccaga tgacacagac tacatcctcc ctgtctgcct ctctgggaga cagagtcacc      60
atcagttgca gggcaagtca ggatattagc aattatttaa actggtatca gcagaaacca    120
gatggaactg ttaaactcct gatctattac acatctagat tatactcagg agtcccatca    180
aggttcagtg gcagtgggtc tgggacagat tattctctca ccatcagcaa cctggaacct    240
aaagatattg ccacttacta ttgtcagcag tttagtgagc ttcctcggac gttcggtgga    300
ggcaccaagc tggaaatcaa a                                                321

<210> SEQ ID NO 82
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 82
gatgtccaga tgacacagac tacatcctcc ctgtctgcct ctctgggaga cagagtcacc      60
atcagttgta gggcaagtca ggatattagc aattatttaa actggtatca gcagaaacca    120
gatggaactg ttaaactcct gatctactac acatcacgat tacactcagg agtcccatca    180
aggttcagtg gcagtgggtc tgggacagat ttttctctca ccatcagcaa cctggaacct    240
gaagatattg ccacttacta ttgtcagcaa tacaataagg ttccgctcac gttcggtggt    300
gggaccaagc tggagctgaa a                                                321

<210> SEQ ID NO 83
<211> LENGTH: 336
<212> TYPE: DNA
<213> ORGANISM: Artificial Sequence
<220> FEATURE:
<223> OTHER INFORMATION: Synthetic polynucleotide

<400> SEQUENCE: 83
gatattgtga tgactcaggc tgcaccctct gtacctgtca ctcctggaga gtcagtttcc      60
atctcctgca ggtctactaa gagtcttctg catttaatg gcaacactta cttgttttgg     120
```

| | |
|---|---|
| ttcctgcaga ggccaggcca gtctcctcag cgcctgatat attatatgtc caaccttgcc | 180 |
| tcaggagtcc cagacaggtt cagtggcaga gggtcaggaa ctgatttcac actgagaatc | 240 |
| agtagagtgg aggctgagga tgtgggtgtt tattactgta tgcaaagtct agaatatcca | 300 |
| ttcacgttcg gcacggggac aaaattggaa ataaaa | 336 |

<210> SEQ ID NO 84
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 84

| | |
|---|---|
| caaattgttc tctcccagtc tccagcaatc ctgtctgcat ctccagggga gaaggtcaca | 60 |
| atgacttgca gggccagttc aagtgtaagt tacatgcact ggtaccagca gaagtcagga | 120 |
| tcctccccca aaccctggat ttatgccaca tccaacctgg cttctggagt ccctgctcgc | 180 |
| ttcagtggca gtgggtctgg gacctcttac tctctcacaa tcagcagagt ggaggctgaa | 240 |
| gatgctgcca cttattactg ccagcagtgg agtagtaacc cacccacgtt cggagggggg | 300 |
| accaagctgg aaataaaa | 318 |

<210> SEQ ID NO 85
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 85

| | |
|---|---|
| gacatccaga tgactcagtc tccagcttcc ctgtctgcat ctgtgggaga aactgtcacc | 60 |
| atcacatgtc gagcaagtga aaatattgac agttatttag catggtatca gcagaaacag | 120 |
| ggaaaatctc ctcagctcct ggtctatgct gcaacactct accagatggg tgtgccatca | 180 |
| aggttcagtg gcagtggatc aggcacacag tattctctca agatcaacag cctgcagtct | 240 |
| gaagatgttg cgagatatta ctgtcaacat tattataata ctccgtggac gttcggtgga | 300 |
| ggcaccaagc tggaaatcaa a | 321 |

<210> SEQ ID NO 86
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 86

| | |
|---|---|
| gacattgtga tgacccagtc tcacaaattc atgtccacat cagtgggaga cagggtcagc | 60 |
| atcacctgca aggccagtca ggatgtgagt agtgctgtag cctggtatca acaaaaacca | 120 |
| gggcaatctc ctaaactcct gatttactgg gcatccaccc ggcacactgg agtccctgat | 180 |
| cgcttcacag gcagtggatc tgggacagat tatactctca ccgtcagcaa tgtgcaggct | 240 |
| gaagacctgg cactttatta ctgtcagcaa cattatatca ctccttacac gttcggaggg | 300 |
| gggaccaagc tggaaataaa a | 321 |

<210> SEQ ID NO 87
<211> LENGTH: 321
<212> TYPE: DNA

<213> ORGANISM: Artificial Sequence
<220> FEATURE:
<223> OTHER INFORMATION: Synthetic polynucleotide

<400> SEQUENCE: 87

```
gacattgtga tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atccgtacac gttcggaggg   300
gggaccaagc tggaaataaa a                                             321
```

<210> SEQ ID NO 88
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 88

Gly Tyr Thr Phe Ser Ser Tyr
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 89

Ser Tyr Trp Ile Tyr
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 90

Asn Pro Thr Thr Gly Tyr
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 91

Gly Tyr Thr Phe Thr Ser Ser
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 92

```
Ser Ser Trp Met His
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 93

His Pro Asn Ser Gly Asn
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 94

Gly Phe Asn Ile Lys Asp Tyr
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 95

Asp Tyr Tyr Met Asn
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 96

Asp Pro Asp Asn Gly Asn
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 97

Gly Tyr Thr Phe Thr Asn Tyr
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 98
```

Asn Tyr Asn Met Asp
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 99

Asn Pro Asn Ser Gly Gly
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 100

Gly Tyr Thr Phe Thr Ser Tyr
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 101

Ser Tyr Trp Met His
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 102

Tyr Pro Gly Ser Gly Arg
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 103

Gly Tyr Ser Ile Thr Ser Asp Phe
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 104

Ser Asp Phe Ala Trp Ser

```
<210> SEQ ID NO 105
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 105

Ser Tyr Ser Gly Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 106

Gly Phe Thr Phe Ser Ser Tyr
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 107

Ser Tyr Gly Met Ser
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 108

Ser Gly Gly Gly Ser Tyr
1               5
```